United States Patent
Jung et al.

(10) Patent No.: US 11,747,341 B2
(45) Date of Patent: Sep. 5, 2023

(54) METHODS OF USE FOR LOW-BIND POLYPROPYLENE PLATES AND VIALS

(71) Applicant: Waters Technologies Corporation, Milford, MA (US)

(72) Inventors: Moon Chul Jung, Waltham, MA (US); Mary Elizabeth Lame, Uxbridge, MA (US); Caitlin Dunning, Norwood, MA (US); Christopher John Hughes, Manchester (GB); Xiaoxiao Liu, Milford, MA (US); Paula Orens, Attleboro, MA (US); Yun Wang Alelyunas, Stow, MA (US); Erin E. Chambers, Sutton, MA (US); David Dao, Worcester, MA (US); Robert Birdsall, Westborough, MA (US)

(73) Assignee: Waters Technologies Corporation, Milford, MA (US)

( * ) Notice: Subject to any disclaimer, the term of this patent is extended or adjusted under 35 U.S.C. 154(b) by 110 days.

(21) Appl. No.: 16/808,233

(22) Filed: Mar. 3, 2020

(65) Prior Publication Data
US 2020/0284802 A1      Sep. 10, 2020

Related U.S. Application Data

(60) Provisional application No. 62/826,534, filed on Mar. 29, 2019, provisional application No. 62/813,257, filed on Mar. 4, 2019.

(51) Int. Cl.
*G01N 33/68* (2006.01)
*G01N 30/06* (2006.01)
*G01N 30/72* (2006.01)

(52) U.S. Cl.
CPC ......... *G01N 33/6848* (2013.01); *G01N 30/06* (2013.01); *G01N 30/7233* (2013.01)

(58) Field of Classification Search
None
See application file for complete search history.

(56) References Cited

U.S. PATENT DOCUMENTS 3,922,392 A    11/1975   Kohlschutter et al.
5,492,730 A     2/1996   Balaba et al.
(Continued)

FOREIGN PATENT DOCUMENTS

EP       2532716 A1    12/2012
WO    2008134399 A1    11/2008
(Continued)

OTHER PUBLICATIONS

Van Midwoud et al. "Comparison of Biocompatibility and Adsorption Properties of Different Plastics for Advanced Microfluidic Cell and Tissue Culture Models." Anal. Chem. 84.9(2012): 3938-3944.
(Continued)

*Primary Examiner* — Xiaoyun R Xu
(74) *Attorney, Agent, or Firm* — WOMBLE BOND DICKINSON (US) LLP; Deborah M. Vernon; Mark R. Deluca

(57) ABSTRACT

The present disclosure relates to a method of analyzing a sample comprising a hydrophobic molecule. The method includes preparing an aqueous solution comprising the sample. The method also includes placing the solution in contact with a polypropylene substrate having a deactivated surface that reduces adsorption of the hydrophobic molecule relative to a polypropylene substrate that has not been deactivated. The method also includes analyzing the sample.

9 Claims, 24 Drawing Sheets

(56) References Cited

U.S. PATENT DOCUMENTS

| | | | |
|---|---|---|---|
| 5,567,235 | A | 10/1996 | Carson et al. |
| 6,235,864 | B1 | 5/2001 | Loy et al. |
| 6,329,487 | B1 | 12/2001 | Abel et al. |
| 6,444,326 | B1 | 9/2002 | Smith |
| 6,479,146 | B1 | 11/2002 | Caruso et al. |
| 6,511,760 | B1 | 1/2003 | Barone et al. |
| 6,548,264 | B1 | 4/2003 | Tan et al. |
| 7,358,300 | B2 | 4/2008 | Sakurai et al. |
| 2005/0169803 | A1 | 8/2005 | Betz et al. |
| 2008/0145276 | A1 | 6/2008 | Betz et al. |
| 2008/0159916 | A1 | 7/2008 | Betz et al. |
| 2018/0033454 | A1 | 2/2018 | Hardek |

FOREIGN PATENT DOCUMENTS

| | | |
|---|---|---|
| WO | 2016100557 A2 | 6/2016 |
| WO | 2016176561 A1 | 11/2016 |
| WO | 2017087032 A1 | 5/2017 |

OTHER PUBLICATIONS

Vials, screw top, silane treated: 27238 Supelco. Retrieved from www.sigmaaldrich.com on Oct. 20, 2015.

Wang et al. "Silica coating on ultrafine a-alumina particles." Mater. Sci. Eng. A 395(2005): 148-152.

Weikart et al. "Plasma-Treated Microplates with Enhanced Protein Recoveries and Minimized Extractables." SLAS Tech. 22.1(2017): 98-105.

Weiß et al. "Eppendorf LoBind®: Evaluation of protein recovery in Eppendorf Protein LoBind Tubes and Plates." Eppendorf: Applications Technical Report. Note 180: Nov. 2010.

Yang et al. "Design of conformal, substrate-independent surface modification for controlled protein adsorption by chemical vapor deposition (CVD)." Soft Matter. 8(2012): 31-43.

Yang et al. "Synergistic Prevention of Biofouling in Seawater Desalination by Zwitterionic Surfaces and Low-Level Chlorination." Adv. MAter. 26(2014): 1711-1718.

Yang et al. "Ultrathin Antifouling Coatings with Stable Surface Zwitterionic Functionality by Initiated Chemical Vapor Deposition (iCVD)." Langmuir. 28(2012): 12266-12274.

Yeh et al. "Modification of Silicone Elastomer with Zwitterionic Silane for Durable Antifouling Properties." Langmuir. 30(2014): 11386-11393.

Zhang et al. "Anti-fouling Coatings of Poly (dimethlysiloxane) Devices for Biological and Biomedical Applications." J. Med. Biol. Eng. 35(2015): 143-155.

Zhang et al. "LC/MS/MS Bioanalytical Protocol for Determining the Degree of Non-Specific Binding in Multi-Well Plates." Q2 Solutions. (2017).

Zhang et al. "Surface modification of stainless steel by grafting of poly(ethylene glycol) for reduction in protein adsorption." Biomater. 22(2001): 1541-1548.

Zhao et al. "Bacterial attachment and removal properties of silicon- and nitrogen-doped diamond-like carbon coatings." Biofouling. 25.5(2009): 377-385.

Friess. "Protein adsorption to vial surfaces—Quantification, structural and mechanistic studies." Ludwig-Maximilians-Universitat Munchen. Jul. 2011.

Kristensen et al. "Adsorption of Cationic Peptides to Solid Surfaces of Glass and Plastic." PLoS One. 10.5(2015): 1-17.

Kroke et al. "Silazane derived ceramics and related materials." Mater. Sci. Eng. 26(2000): 97-199.

Kumar et al. "Amphiphilic Copolymer Coatings via Plasma Polymerisation Process: Switching and Anti-Biofouling Characteristics." Plasma Process. Polym. 8(2011): 373-385.

Kumar et al. "Fluorocarbon Coatings Via Plasma Enhanced Chemical Vapor Deposition of 1H,1H,2H,2H-perfluorodecyl Acrylate—2, Moprhology, Wettability and Antifouling Characterization." Plasma Process. Polym. 7(2010): 926-938.

Lasseter et al. "Covalently Modified Silicon and Diamond Surfaces: Resisting to Nonspecific Protein Adsorption and Optimization for Biosensing." J Am. Chem. Soc. 126(2004): 10220-10221.

Le et al. "Evaluation of Different Nonspecific Binding Blocking Agents Deposited Inside Poly(methyl methacrylate) Microfluidic Flow-Cells." Langmuir. 27(2011): 9043-9051.

Lee et al. "Mussel-Inspired Surface Chemistry for Multifunctional Coatings." Science. 318(2007): 426-430.

Lee et al. "Protein patterning utilizing region-specific control of wettability by surface modification under atmospheric pressure." Appl. Phys. Lett. 103(2013): 123701.

Li et al. "Carbon Dioxide Mediated Synthesis of Mesoporous Silica Films: Tuning Properties using Pressure." Chem. Mater. 20.9(2008): 3229-3238.

Li et al. "Protein Adsorption on Oligo(ethylene glycol)-Terminated Alkanethiolate Self-Assembled Monolayers: The Molecular Basis for Nonfouling Behavior." J. Phys. Chem. B. 109(2005): 2934-2941.

Liu et al. "Comment on Electrodeposited Silicate Films: Importance of Supporting Electrolyte." Anal. Chem. 81.8(2009): 3199-3200.

Maes et al. "Strategies to reduce aspecific adsorption of peptides and proteins in liquid chromatography-mass spectrometry based bioanalyses: An overview." J. Chromatogr. A. 1358(2014): 1-13.

Mak et al. "Influence of Different Polyelectrolytes on Layer-by-Layer Microcapsule Properties: Encapsulation Efficiency and Colloidal and Temperature Stability." Chem. Mater. 20(2008): 5475-5484.

Masuda et al. "Liquid-Phase Patterning and Microstructure of Anatase Ti)2 Films on Sn)2:F Substrates Using Superhydrophilic Surface." Chem. Mater. 20(2008): 1057-1063.

McCalley. "Effect of buffer on peak shape of peptides in reversed-phase high performance liquid chromatography." J. Chromatogr. A. 1038(2004): 77-84.

Mi et al. "Integrated Antimicrobial and Nonfouling Zwitterionic Polymers." Angew. Chem. Int. Ed. 53(2014): 1746-1754.

Mitsuishi et al. "Preparation of Ultrathin Silsesquioxane Nanofilms via Polymer Langmuir—Blodgett Films." Chem. Mater. 20(2008): 4310-4316.

Muguruma et al. "Protein patterning on functionalized surface prepared by selective plasma polymerization." Surface Coatings Tech. 205(2010): 2490-2494.

Mulvaney et al. "Silica encapsulation of quantum dots and metal clusters." J. Mater, Chem. 10(2000): 1259-1270.

Naslain. "Ceramic Matrix Composites." Materials Synthesis and Processing, European White Book on Fundamental Research in Materials. Chapter 6.6. (1987): 213-217.

Navabpour et al. "Optimisation of the properties of siloxane coatings as anti-biofouling coatings: Comparison of PACVD and hybrid PACVD-PVD coatings." Surface Coatings Tech. 204(2010): 3188-3195.

Navarro et al. "Biomaterials in orthopaedics." J. R. Soc. Interface. 5(2008): 1137-1158.

Nikolic et al. "Alumina strengthening by silica sol-gel coating." Thin Solid Films. 295(1997): 101-103.

Nisol et al. "Atmospheric plasma synthesized PEG coatings: nonfouling biomaterials showing protein and cell repulsion." Surface Coatings Tech. 252(2014): 126-133.

Nomura et al. "Sum-frequency generation analyses of the structure of water at amphoteric SAM-liquid water interfaces." Colloids Surfaces B Biointerfaces. 121(2014): 264-269.

Ogawa et al. "Deposition of Thin Nanoporous Silica Layers on Solid Surfaces." Chem. Mater. 18.7(2006): 1715-1718.

Ostuni et al. "A Survey of Structure—Property Relationships of Surfaces that Resist the Adsorption of Protein." Langmuir. 17(2001): 5605-5620.

Pallandre et al. "Binary Nanopatterned Surfaces Prepared from Silane Monolayers." Nano Lett. 4.2(2004): 365-371.

Perullini et al. "Optimizing Silica Encapsulation of Living Cells: In Situ Evaluation of Cellular Stress." Chem. Mater. 209(2008): 3015-3021.

Pidhatika et al. "Nonfouling Surface Coatings Based on Poly(2-methyl-2-oxazoline)." Chimia. 62.4(2008): 264-269.

(56) References Cited

OTHER PUBLICATIONS

Plasma Deposition: SiO2 Medical Products. Retrieved from www.sio2med.com on Oct. 20, 2015.
ProteoSave™: Sbio. Retrieved from s-bio.com on Oct. 20, 2015.
Protivinsky et al. "Effect of chemically modified titanium surfaces on protein adsorption and osteoblast precursor cell behavior." Int. J. Oral Maxillofacial Implants. 22.4(2007): 542-550.
Pulker. Coatings on Glass. Elsevier B. V. (1999).
Sanchez et al. "Design, Synthesis, and Properties of Inorganic and Hybrid Thin Films Having Periodically Organized Nanoporosity." Chem. Mater. 20(2008): 682-737.
Sardella et al. "Control of cell adhesion and spreading by spatial microarranged PEO-like and pdAA domains." Surface Coatings Tech. 200(2005): 51-57.
Schlenoff et al. "Zwitteration: Coating Surfaces with Zwitterionic Functionality to Reduce Nonspecific Adsorption." Langmuir. 30.32(2014): 9625-9636.
Schmidt et al. "Colloidal Gelation as a General Approach to the Production of Porous Materials." Chem. Mater. 20.9(2008): 2851-2853.
Schottner. "Hybrid Sol-Gel-Derived Polymers: Applications of Multifunctional Materials." Chem. Mater. 13(2001): 3422-3435.
Segro et al. "Solvent-resistant sol-gel polydimethyldiphenylsiloxane coating for on-line hyphenation of capillary microextraction with high-performance liquid chromatography." J. Chromatogr. A. 1205(2008): 26-35.
Shao et al. "Molecular Understanding and Design of Zwitterionic Materials." Adv. Mater. 27(2015): 15-26.
Shen et al. "Heterogeneous surfaces to repel proteins." Adv. Colloid Interface Sci. 228(2016): 40-54.
Shirahata et al. "Ultrathin Poly(ethylene glycol) Monolayers Formed by Chemical Vapor Deposition on Silicon Substrates." J. Nanosci. Nanotech. 6(2006): 1695-1700.
Shyong et al. "Evaluation of Coated Microplates for Stability and Recovery of Therapeutic Proteins and Peptides." Merck. 2017.
Silanized Glass Vials: EP Scientific Products. Retreived from www.thomassci.com on Oct. 20, 2015.
Silanized Vials. Glass Vials—SS2. Retreived from glassvials.com on Oct. 20, 2015.
SiliGuard™ & Silanized Low-bind Collection Plates, Vials & Inserts: Advantage™ 1mL 96-Well Collection Plates. Retrieved from www.analytical-sales.com on Oct. 20, 2015.
Stejskal et al. "Suppression of Peptide Sample Losses in Autosampler Vials." J. Proteome. 12(2013): 3057-3062.
Sulaiman et al. "Molecules with Perfect Cubic Symmetry as Nanobuilding Blocks for 3-D Assemblies. Elaboration of Octavinylsilsequioxane. Unusual Luminescence Shifts May Indicate Extended Conjugation Involving the Silsesquioxane Core." Chem. Mater. 20(2008): 5563-5573.
Trujillo et al. "Grafted Functional Polymer Nanostructures Patterned Bottom-Up by Colloidal Lithography and Initiated Chemical Vapor Deposition (iCVD)." Chem. Mater. 21(2009): 742-740.
"Corning® and Falcon® Microplates Selection Guide: For Assys and Drug Delivery." Mar. 2015.
"Dursan® Coating Improves Medical Device Performance and Safety." SilcokTek. Retrieved from www.silcotek.com on Oct. 21, 2015.
"LoBind." Eppendorf Consumables. 2009.
"Non Binding Microplates: Microplates with ultra-low binding surface." greiner bio-one. Revised May 2013.
"Non Binding Microplates: Solid bottom microplates with ultra-low binding surface." greiner bio-one. Revised Sep. 2007.
"Silanized Glass Vials: Deactivation Methods." Chromacol Product Guide. 2015.
"The Chromacol SCI-VI™ System Microsampling Vials and Sleeves." Chromacol Product Brief PB02-07-UK. 2015.
"The Complete Guide of Autosampler Vials, Caps & Inserts." MicroSolv™. (2010).

"Understanding Deactivating or Silanizing Glass Vial & Insert Surfaces for Chromatography." KB: Knowledge Base. Retrieved from kb.mtc-usa.com on Oct. 20, 2015.
Aksakal et al. "Biceramic dip-coating on Ti-6A1-4V and 316L SS implant materials." J. Mater. Sci: Mater. Med. 19(2008):2097-2104.
Alhooshani et al. "Sol-gel approach to in situ creating of high pH-resistant surface-bonded organic-inorganic hybrid zirconia coating for capillary microextraction (in-tube SPME)." J. Chromatogr. A. 1062(2005): 1-14.
Aliev et al. "Porous silica and polysilsesquioxane with covalently linked phosphonates and phosphonic acids." J. Mater. Chem. 10(2000): 2758-2764.
Bahloul et al. "Pyrolysis chemistry of polysilazane precursors to silicon carbonitride. Part 1.—Thermal degradation of the polymers." J. Mater. Chem. 7.1(1997): 109-116.
Barnes et al. "Synthesis and Hydrolytic Stability of Some Organosilicon Phosphonate Esters." Some Organosilicon Phosphonate Esters. 25(1960): 1191-1194.
Baxamusa et al. "Protection of Sensors for Biological Applications by Photoinitiated Chemical Vapor Deposition of Hydrogel Thin Films." Biomacromol. 9(2008): 2857-2862.
Baxamusa et al. "Random Copolymer Films with Molecular-Scale Compositional Heterogeneities that Interfere with Protein Adsorption." Adv. Functi. Mater. 19(2009): 3489-3496.
Bobály et al. "Challenges in liquid chromatographic characterization of proteins." J. Chromatogr. B. 1032(2016): 3-22.
Bose et al. "Initiated chemical vapor deposition of poly(2-hydroxyethyl methacrylate) hydrogels." Thin Solid Films. 519(2011): 4415-4417.
Brétagnol et al. "Functional Micropatterned Surfaces by Combination of Plasma Polymerization and Life-Off Processes." PLasma Process. Polym. 3(2006): 30-38.
Brétagnol et al. "Micro-patterned surfaces based on plasma modification of PEO-like coating applications." Sensors Actuators B. 123(2007): 283-292.
Cecchet et al. "One Step Growth of Protein Antifouling Surfaces: Monolayers of Poly(ethylene oxide) (PEO) Derivatives on Oxidized and Hydrogen-Passivated Silicon Surfaces." Langmuir. 22(2006): 1173-1181.
Chapman et al. "Polymeric Thin Films That Resist te Adsorption of Proteins and the Adhesion of Bacteria." Langmuir. 17(2001): 1225-1233.
Chapman et al. "Surveying for Surfaces that Resist the Adsorption of Proteins." J. Am. Chem. Soc. 122(2000): 8303-8304.
Chen et al. "A New Avenue to Nonfouling Materials." Adv. Mater. 20(2008): 335-338.
Chen. "II. Thin Film Desposition." Harvard University: Applied Physics 298r. Apr. 12, 2004.
Cheng et al. "Photopatterning of self-assembled poly (ethylene) glycol monolayer for neuronal network fabrication." J. Neuro. Meth. 213(2013): 196-203.
Chester et al. "Pressure-regulating fluid interface and phase behavior considerations in the coupling of packed-column supercritical fluid chromatography with low-pressure detectors." J. Chromatogr. A. 807(1998): 265-273.
Chien et al. "The potential of nano-structured silicon oxide type coatings deposited by PACVD for control of aquatic biofouling." Biofouling. 25.1(2009): 55-67.
Choi et al. "Fabrication and Characterization of Plasma-Polymerized Poly(ethylene glycol) Film with Superior Biocompatibility." ACS Appl. Mater. Interfaces. 5(2013): 697-702.
Courtois et al. "A study of surface modicaition and anchoring techniques used in the preparation of monolithic microcolumns in fused silica capillaries." J. Sep. Sci. 29(2006): 14-24.
Darling. "Physical Vapor Deposition: Lecture Notes: 520/530/580. 495 Film Desposition." www.engr.washington.edu/~cam/PROCESSES/physicalvapdeppdf.html Fall 2003.
Deng et al. "Self-Assembled Monolayers of Alkanethiolates Presenting Tri(propylene sulfoxide) Groups Resist the Adsorption of Protein." J. Am. Chem. Soc. 118(1996): 5136-5137.

(56) References Cited

OTHER PUBLICATIONS

Emoto et al. "Preparation of non-fouling surface through the coating with core-polymerized block copolymer micelles having aldehyde-ended PEG shell." Colloids. Surfaces B. Bionterfaces. 18(2000): 337-346.
Freitag. "Ceramic Matrix Composites: Chapter 2.4." Opportunities for Advanced Ceramics to Meet the Needs of the Industraies of the Future. (1998):2-14.
Krishnan et al. "Diffusion Coatings for Corrosion Resistant Components in Coal Gasification Systems." U.S. Department of Energy, SRI Project PYU-13063. Technical Progress Report. Jan. 2005.
Goebel-Stengel et al. "The importance of using the optimal plastic and glassware in studies involving peptides." Anal. Biochem. 414. 1(2011): 38-46.
Haynes et al. "High-Temperature Diffusion Barriers for Protective Coatings." Oak Ridge National Laboratory. (2004).
Holmlin et al. "Zwitterionic SAMs that Resist Nonspecific Adsorption of Protein from Aqueous Buffer." Langmuir. 17(2001):2841-2850.
Horvath et al. "Polymer wall coatings for capillary electrophoresis." Electrophoresis. 22(2001): 644-655.
Hsieh et al. "Effective Enhancement of Fluorescence Detection Efficiency in Protein Microarray Assays: Application of a Highly Fluorinated Organosilane as the Blocking Agent on the Background Surface by a Facile Vapor-Phase Deposition Process." Anal. Chem. 81(2009): 7908-7916.
Huang et al. "Zwitterionic Polymer-Based Platform with Two-Layer Architecture for Ultra Low Fouling and High Protein Loading." Anal. Chem. 84(2012): 3440-3445.
Huang et al. "Coating of poly(dimethylsilonxane) with n-dodecyl-β-D-maltoside to minimize nonspecific protein adsorption." Lab Chip. 5(2005): 1005-1007.
Huang et al. "In Situ Surface Tailoring with Zwitterionix Carboxybetaine Moieties on Self-Assembled Thin Film for Anitfouling Biointerface." Materials. 7(2014): 130-142.
Jing et al. "Cell patterning using molecular vapor deposition of self-assembled monolayers and lift-off technique." Acta Biomater. 7(2011): 1094-1103.
Kanamori et al. "Thick silica gel coatings on methylsilsesquioxane monoliths using anistropic phase separation." J. Sep. Sci. 2992006): 2463-2470.
Kanari et al. "Protein Adsorption o Self-Assembed Monolayers Induced by Surface Water Molecule." Jpn. J. Appl. Phys. 46.9B(2007): 6303-6308.
Kaplan. "The Best Kept Secret in Industry." Presented at the "Ninth International Symposium on Polymer Surface Modification: Relevance to Adhesion." Jun. 17-18, 2013.
Khan et al. "Integrated Microreactor for Continuous Colloid Synthesis and Surface-Coating." 10th International Conference on Miniaturized Systems for Chemistry and Life Sciences (mTAS2006). Nov. 5-9, 2006, Tokyo, Japan.
Kim et al. "High pH-resistant, surface-bonded sol-gel titania hybrid organic-inorganic coating for effective on-line hyphenation of capillary microextraction (in-tbe solid-phase microextraction) with high-performance liquid chromatography." J. Chromatogr. A. 1047(2004): 165-174.

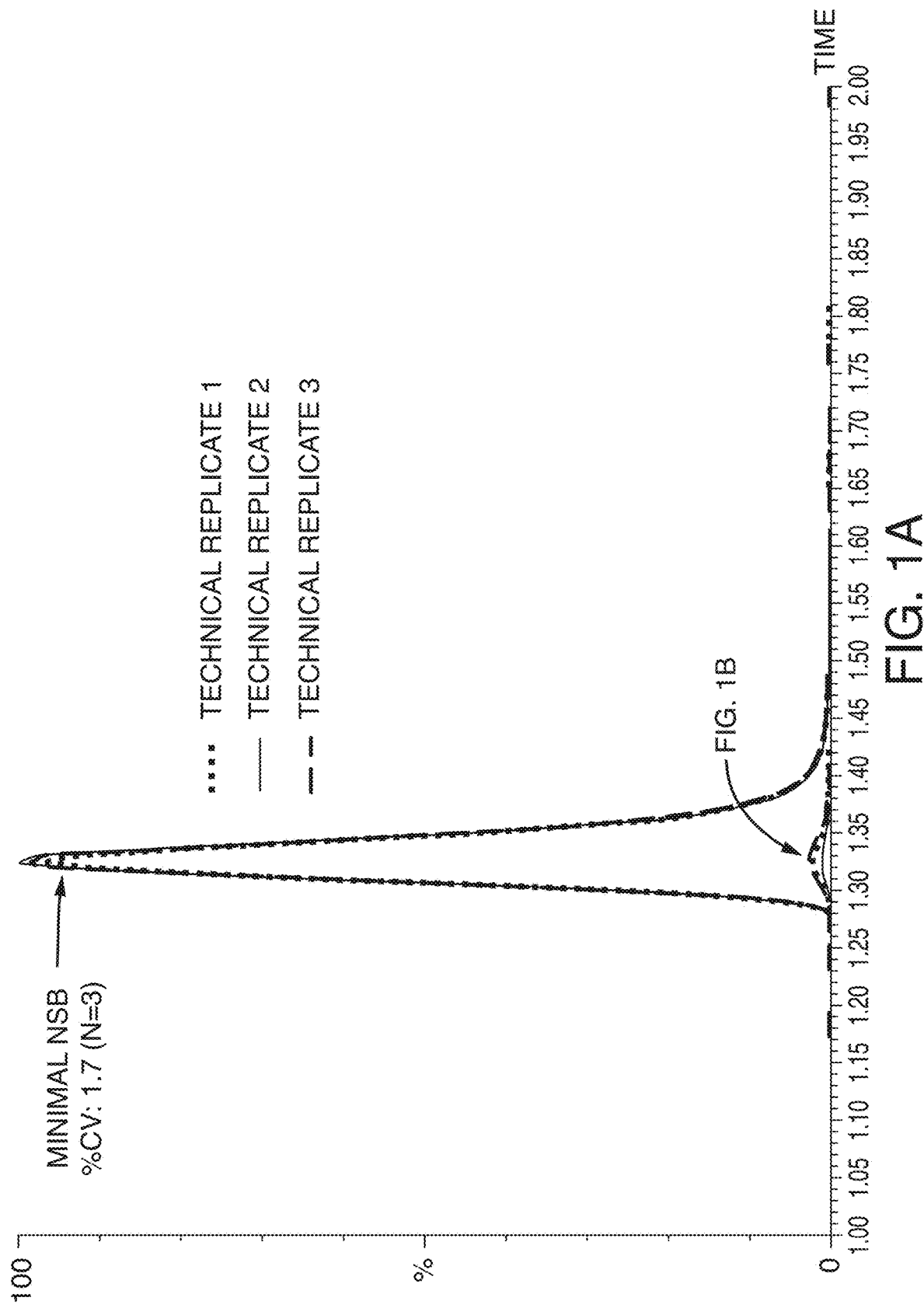

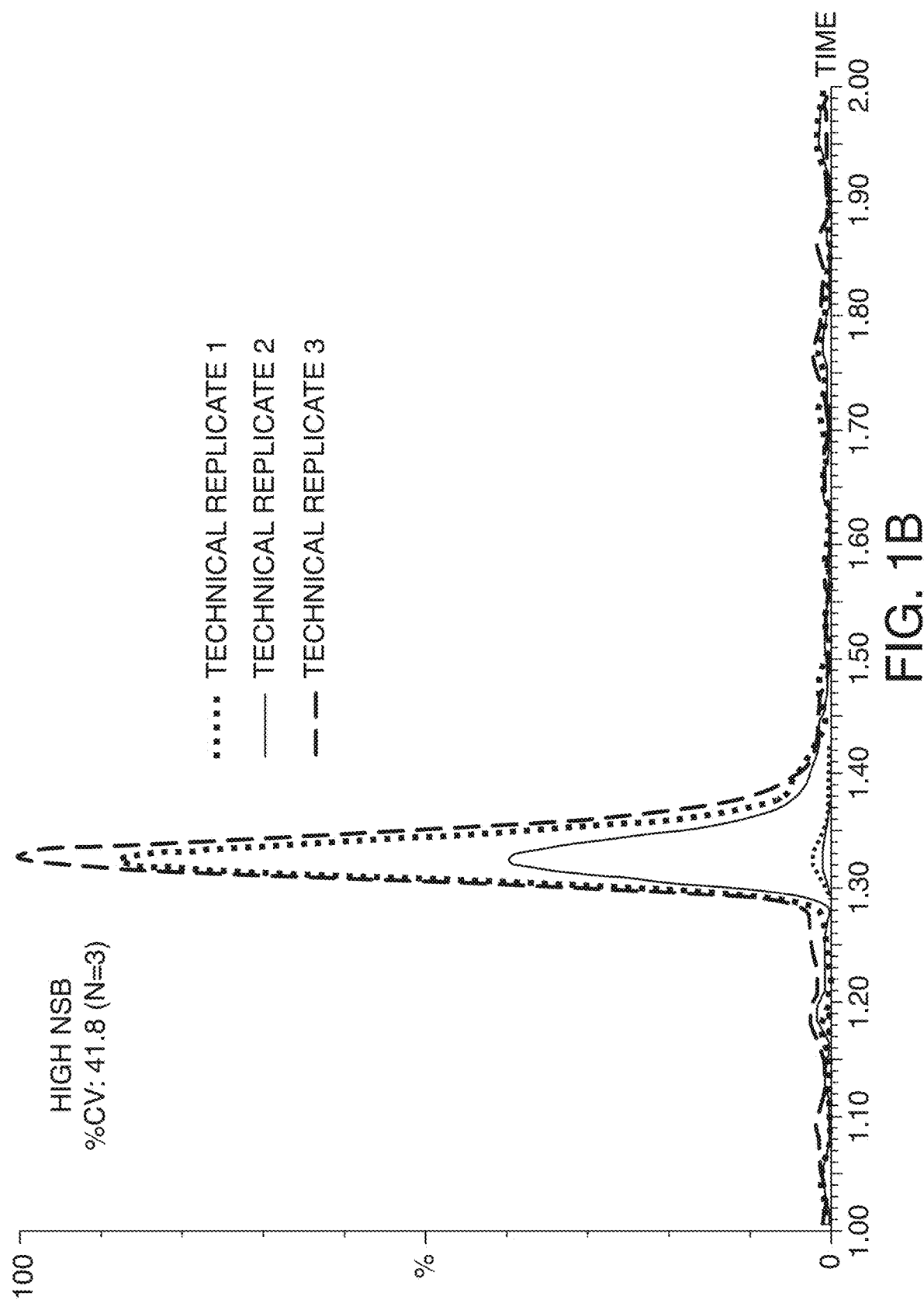

METHODS OF USE FOR LOW-BIND POLYPROPYLENE PLATES AND VIALS

CROSS-REFERENCE TO RELATED APPLICATIONS

This application claims priority to and benefit of U.S. provisional patent application No. 62/813,257, filed on Mar. 4, 2019 and entitled "Methods of Use for Low-Bind Polypropylene Plates and Vials" the entire contents of which are hereby incorporated by reference. This application also claims priority to and benefit of U.S. provisional patent application No. 62/826,534, filed on Mar. 29, 2019 and entitled "Methods of Use for Low-Bind Polypropylene Plates and Vials" the entire contents of which are hereby incorporated by reference.

FIELD OF THE TECHNOLOGY

The present disclosure relates to methods of use for low-bind polypropylene plates and vials. More specifically, the present disclosure relates to placing a solution having a hydrophobic molecule in contact with a polypropylene substrate having a deactivated surface that reduces adsorption of the hydrophobic molecule relative to a polypropylene substrate that has not been deactivated.

BACKGROUND

Successfully quantitating hydrophobic molecules, for example, proteins and peptides, with liquid chromatography-mass spectrometry (LC-MS) is often more challenging than a similar task for small molecules. The large and complex structures of proteins and peptides not only require a different approach to LC-MS method development, but can cause other unique problems such as nonspecific adsorption (or nonspecific binding). Proteins and peptides in solution tend to stick to the surfaces they encounter, such as LC-MS fluidic paths, LC column packings, and even sample containers. Such losses do not just negatively impact the assay sensitivity, but also compromise the reproducibility, precision, and accuracy of the analysis.

Small molecules can stick to these surfaces as well, but their surface adhesion is typically driven by a single attraction mechanism and can be dealt with in a straightforward manner. For example, one can choose a polymeric container for a highly basic analyte instead of a glass container that bears acidic silanol groups on the surface. For proteins and peptides, however, the picture is more complicated. They may form multiple interactions with exposed surfaces through various chemical attraction mechanisms. The more protein or peptides the sample contains, the bigger the challenge is. It is therefore not trivial to find a single sample storage condition that prevents the loss of all proteins, peptides, or hydrophobic molecules (including small molecules), of interest.

A widely used alternative approach to avoid these losses is to add blocking agents such as surfactants or carrier proteins to the sample, or preconditioning the surfaces. Preconditioning is an extra step that often produces irreproducible results. Although highly effective in general, adding blocking agents to the sample creates more complexity in downstream LC-MS analyses by presenting extra peaks in chromatograms of MS spectra or by inducing ion suppression or enhancement. Therefore, using blocking agents is not always the best tactic unless it is absolutely necessary.

SUMMARY

The present technology provides for maximum recovery of hydrophobic molecules, including proteins, peptides, and hydrophobic small molecules, without using blocking agents. The present technology uses deactivated polypropylene plates and vials. The deactivated polypropylene surface is less hydrophobic (or more hydrophilic) than the polypropylene surface that is not deactivated. The deactivated surface reduces adsorption of the hydrophobic molecule relative to a polypropylene substrate that has not been deactivated. In this way, recovery of hydrophobic molecules, including proteins, peptides, and hydrophobic small molecules, can be maximized, e.g., recovery of hydrophobic molecules can be between 75% and 100%.

In one aspect, the technology relates to a method of analyzing a sample comprising a hydrophobic molecule. The method includes preparing an aqueous solution comprising the sample. The method also includes placing the solution in contact with a polypropylene substrate having a deactivated surface that reduces adsorption of the hydrophobic molecule relative to a polypropylene substrate that has not been deactivated. The method also includes analyzing the sample. The method can include one or more of the embodiments described herein.

In some embodiments, the hydrophobic molecule is a biomolecule. The biomolecule can be a protein or a peptide or a fatty acid.

In some embodiments, the deactivated surface is more hydrophilic than the polypropylene substrate without a deactivated surface. The deactivated surface can be less hydrophobic than the polypropylene substrate without a deactivated surface. In some embodiments, the polypropylene substrate having the deactivated surface is a vial or plate.

In some embodiments, the method also includes separating the sample with liquid chromatography. The sample can be analyzed after separation with liquid chromatography.

In some embodiments, the aqueous solution also includes acetonitrile and an acid. The aqueous solution can include an 80:20 water:acetonitrile solution. The acid can be trifluoroacetic acid or formic acid.

In another aspect, the technology relates to a method of analyzing a sample comprising a hydrophobic molecule. The method includes preparing an aqueous solution comprising the sample. The method also includes placing the solution in contact with a polypropylene substrate having a deactivated surface that is more hydrophilic than the polypropylene substrate without a deactivated surface. The method also includes analyzing the sample. The method can include one or more of the embodiments described herein.

In some embodiments, the hydrophobic molecule is a biomolecule. The biomolecule can be a protein or a peptide or a fatty acid.

In some embodiments, the polypropylene substrate having the deactivated surface is a vial or plate. The method can also include separating the sample with liquid chromatography.

In some embodiments, the aqueous solution further comprises acetonitrile and an acid. The acid can be trifluoroacetic acid or formic acid.

In some embodiments, the hydrophilicity of the surface is measured by contact angle.

In another aspect, the technology relates to a method of analyzing a sample comprising a hydrophobic molecule. The method includes preparing an aqueous solution comprising the sample and between about 0% to about 30% acetonitrile. The method also includes placing the solution in contact with a polypropylene substrate having a deactivated surface. The sample is separated using liquid chromatography and the sample is analyzed. The method has between about 75% to about 100% recovery. The method can include one or more of the embodiments described herein.

In some embodiments, the aqueous solution contains between about 5% to about 30% acetonitrile and the recovery is about 80% to about 100%. In some embodiments, the recovery is between about 90% to about 100%. The aqueous solution can include about 20% acetonitrile. In some embodiments, the aqueous solution also includes 0.2% trifluoroacetic acid.

In another aspect, the technology relates to a method of analyzing a protein. The method includes preparing an aqueous solution comprising the protein, wherein a concentration of the protein is less than about 1 µM. The solution is stored in a polypropylene plate or vial having a deactivated surface. The method also includes analyzing the stored solution using a mass spectrometer, wherein the recovery of the protein is greater than about 90%. The method can include one or more of the embodiments described herein.

In some embodiments, the concentration of the protein is less than about 5 nM.

In some embodiments, the method also includes separating the aqueous solution using liquid chromatography.

The solution can be stored at a temperature less than about room temperature. In some embodiments, the solution is stored in the polypropylene plate or vial having a deactivated surface for about 24 hours. The solution can be stored in the polypropylene plate or vial having a deactivated surface for about 48 hours or about 72 hours. In some embodiments, the solution can be stored in the polypropylene plate or vial for between about 24 hour to about 72 hours. In some embodiments, the solution can be stored in the polypropylene plate or vial for greater than 72 hours.

In another aspect, the technology includes analyzing a peptide. The method includes preparing an aqueous solution comprising the peptide, wherein a concentration of the peptide is less than about 1 µM. The method also includes storing the solution in a polypropylene plate or vial having a deactivated surface and analyzing the stored solution using a mass spectrometer, wherein the recovery of the peptide is greater than about 90%. The method can include one or more of the embodiments described herein.

In some embodiments, the concentration of the protein is less than about 5 nM.

In some embodiments, the method also includes separating the aqueous solution using liquid chromatography.

The solution can be stored at a temperature less than about room temperature. In some embodiments, the solution is stored in the polypropylene plate or vial having a deactivated surface for about 24 hours. The solution can be stored in the polypropylene plate or vial having a deactivated surface for about 48 hours or about 72 hours. In some embodiments, the solution can be stored in the polypropylene plate or vial for between about 24 hour to about 72 hours. In some embodiments, the solution can be stored in the polypropylene plate or vial for greater than 72 hours.

In another aspect, the technology relates to a method of analyzing a sample comprising a hydrophobic molecule of interest. The method includes preparing an aqueous solution comprising the hydrophobic molecule of interest, wherein a concentration of the hydrophobic molecule of interest is less than about 1 µM. The method also includes placing the solution in contact with a surface of a polypropylene substrate, wherein the surface has been treated to reduce adsorption of the hydrophobic molecule of interest as compared to a non-treated surface. The sample is analyzed using mass spectrometry with respect to the hydrophobic molecule of interest. The method can include one or more of the embodiments described herein.

In some embodiments, the hydrophobic molecule of interest is a protein, a peptide, a fatty acid, or combinations thereof.

In some embodiments, the reduction of adsorption of the hydrophobic molecule of interest is provided by a reduction in water contact angle. The water contact angle can be reduced by at least about 1 degree. The water contact angle can be reduced by between about 2 degrees to about 10 degrees. In some embodiments, the reduced water contact angle is about 88 degrees. The reduced water contact angle can be less than about 85 degrees.

In some embodiments, the hydrophobic molecule of interest is provided by an increased in hydrophilicity. The hydrophilicity can be increased by about 40%. In some embodiments, the hydrophilicity is increased by about 50% to about 75%.

BRIEF DESCRIPTION OF THE DRAWINGS

The technology will be more fully understood from the following detailed description taken in conjunction with the accompanying drawings, in which:

FIG. 1A and FIG. 1B are graphs showing a comparison of leuprolide LC-MS/MS peaks (n=3) with and without mitigating NSB. Note that the y-axis scales are not equal for the two panels: the scales are 1:50, also signifying the leuprolide losses if NSB is not properly mitigated

DETAILED DESCRIPTION

Figure 2:
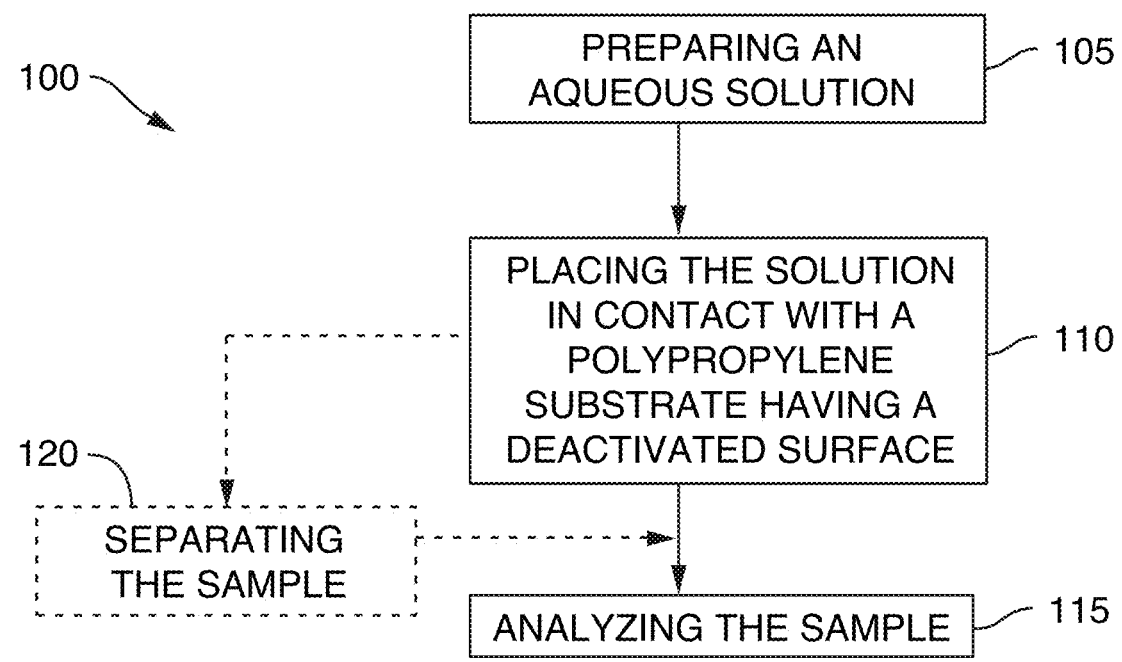
FIG. 2 is a flow chart of a method of analyzing a sample comprising a hydrophobic molecule, according to an illustrative embodiment of the technology.

Quantitative LC-MS assays strive to have high selectivity to accurately detect and identify analytes of interest, high sensitivity to precisely quantify the analytes at a very low concentration, and high reproducibility to ensure that the results can be trusted. While recent advancements in sample preparation methods and LC-MS technologies continue to push the envelope, the demand for greater selectivity, sensitivity, and reproducibility is growing at an even faster pace due to increasing sample complexity and decreasing detection limits. It has become difficult to develop a successful LC-MS assay method unless the whole workflow is scrutinized and optimized accordingly. One crucial, yet often overlooked step, which significantly influences assay sensitivity and reproducibility is sample storage before LC-MS analyses. Analytes can stick to the surface of sample containers and never be recovered. These losses may not be recognized unless the data are carefully compared in a controlled manner. Such surface adsorption, and the consequent analyte loss, is referred to as nonspecific binding (NSB) or nonspecific adsorption (NSA).

The most obvious sign of NSB in a sample container is reduced peak area and consequent poor assay sensitivity. A less readily noticed by equally detrimental outcome of NSB is increased assay variability. FIG. 1A and FIG. 1B show example chromatograms of samples containing the peptide leuprolide (MW 1209.4), which were prepared with and without mitigating NSB. When there was NSB, the variation in triplicate leuprolide peak areas was as high as 41.8% CV. When leuprolide was not lost from NSB, the peaks were 50 times larger and the variability decreased significantly to only 1.7% CV. Finding this issue during method development prevents a serious problem, but finding this issue at a later stage cause more trouble because this can require re-developing and re-validating the assay method. Failure to mitigate NSB early enough can thus lead to a significant waste of time and resources.

Nonspecific binding can occur at any surface that the analyte molecule has a chemical affinity. Sample containers are not the only place where NSB happens. The two most common mechanisms for NSB are ionic interactions and attractions based on polarity. Once the interaction mechanism is identified, the NSB can be effectively mitigated by weakening the chemical affinity between the analyte molecule and the surface, for example by increasing the organic content in sample solutions or changing the solution pH. This approach alone works well with relatively simple small molecules because their NSB is typically driven by a single attraction mechanism at a single functional site. In contrast, larger and more complex molecules, such as proteins and peptides, can form multiple heterogeneous affinity interactions with the surface to promote adsorption. Changing the composition of sample solutions can weaken one or two affinity mechanisms but may not affect all forms of attraction. In addition, some folded proteins can change conformation upon binding to a surface, forming additional affinity interactions and further strengthening the surface adhesion. It is more difficult to detach such deformed and adsorbed proteins, and therefore it is most effective to prevent NSB before it happens.

Another strategy to mitigate NSB is coating the surface with something stickier ('blocking agent') so that the less sticky analytes of interest do not bind to the surface. This is a popular approach to mitigate NSB of proteins and peptides because this technique interferes with various attraction mechanisms simultaneously by placing a blocking barrier between the surface and analyte molecules. Common blocking agents are large polymers, detergents such as Tween-20 and Triton X-100, and carrier proteins such as serum albumin, casein, and plasma. While generally effective, polymers and detergents are detrimental to LC-MS analyses because they can change column selectivity and induce ion suppression. They can also be extremely difficult to remove from columns and LC-MS systems, shortening column life and requiring frequent system maintenance. A carrier protein is a more LC-MS friendly blocking agent, but it is not without any shortcomings. It adds unwanted complexity back into samples. This can complicate the LC-MS baseline of full scan or untargeted methods while indirectly affecting targeted SRM (selected reaction monitoring) methods through ion suppression. Carrier proteins can also behave as mild surfactants in aqueous solutions to form froth, making it difficult to precisely pipet the solutions. Some biological samples contain endogenous components that can act as carrier proteins. Their concentrations can vary among samples from different origins (matrix, species, disease state, etc.) or samples treated with different upstream sample preparation methods. This variation introduces extra assay variability. There are some cases where a carrier protein is necessary, but it is far more desirable to prepare protein or peptide samples without one.

It is not trivial to mitigate protein and peptide NSB by changing the composition of sample solutions alone. The effort, however, can be greatly assisted by using a container that has an inert surface. One example is using a deactivated (or silanized) glass container for a moderately basic analyte, instead of using a glass container that has a high surface silanol activity. For more strongly basic analytes, a polypropylene container with a pure hydrocarbon surface can work better than deactivated glass containers. Some proteins and peptides bind to glass surfaces via ionic attraction between their basic surface groups and the silanol groups on the surface of the glass. Such NSB is more common with proteins and peptides, especially when they are large and complex. This is because some complex proteins and peptides have multiple basic surface groups, even though their overall pH is lower than 7. It is therefore recommended to use polypropylene containers for protein and peptide samples to prevent ionic NSB. However, the hydrocarbon-rich surface of polypropylene is more likely to induce hydrophobicity-based attraction, promoting NSB for hydrophobic molecules. To address this challenge, deactivated polypropylene vials and plates can be used for protein and peptide applications. Deactivated polypropylene vials and plates can be made with high-purity polypropylene and designed to suppress hydrophobic NSB. These deactivated polypropylene plates and vials can increase analyte recovery, sensitivity and reproducibility by minimizing analyte-surface interactions that can lead to sample losses.

The present technology provides methods for maximizing the recovery of hydrophobic molecules, including proteins, peptides, and hydrophobic small molecules, without using blocking agents. Deactivated polypropylene surfaces are less hydrophobic (or more hydrophilic) than the polypropylene surface that is not deactivated. The deactivated surface reduces adsorption of the hydrophobic molecule relative to a polypropylene substrate that has not been deactivated. In this way, recovery of hydrophobic molecules, including proteins, peptides, and hydrophobic small molecules, can be maximized.

FIG. 2 shows a flow chart of a method 100 of analyzing a sample comprising a hydrophobic molecule. The hydrophobic molecule can be a hydrophobic small molecule. The hydrophobic molecule can be a biomolecule, for example, a protein or a peptide or a fatty acid. The hydrophobic molecule can have a concentration in the sample of less than about 100 ng/mL, less than about 1 ng/mL or less than about 1 pg/mL. For example, the concentration of the hydrophobic molecule can be 100 ng/mL, 90 ng/mL, 80 ng/mL, 70 ng/mL, 60 ng/mL, 50 ng/mL, 40 ng/mL, 30 ng/mL, 20 ng/mL, 10 ng/mL, 5 ng/mL, or 1 ng/mL.

The method 100 includes preparing an aqueous solution 105 comprising the sample. The aqueous solution can include acetonitrile and an acid. In some embodiments, the aqueous solution comprises an 80:20 water:acetonitrile solution. Other embodiments of the technology has an aqueous solution with 10:90, 20:80, 30:70, 40:60, 50:50, 60:40, 70:30, or 90:10 water:acetonitrile. The acid can be trifluoroacetic acid (TFA) or formic acid (FA). The aqueous solution can comprise 20% acetonitrile and 0.2% TFA. In some embodiments, the aqueous solution includes the sample and between about 0% to about 30% acetonitrile. In other embodiments, the aqueous solution includes the sample and between about 5% to about 30% acetonitrile. For example, the aqueous solution can include 5%, 10%, 15%, 20%, 25% or 30% acetonitrile. Other solvents can be used in the method, for example, methanol, ethanol, 2-propanol, acetone, tetrahydrofuran (THF), dimethylsulfoxide (DMSO), dimethylformamide (DMF), dimethylacetamide (DMAc), as well as other solvents that are commonly used for chromatographic sample prep and known to those of skill in the art. Other acids can also be used, for example, acetic acids and their derivatives and salts such as difluoroacetic acid, trifluoroacetic acid, chlorinated acetic acids; other carboxylic acids such as citric acid; inorganic acids such as sulfonic acid, phosphoric acid, nitric acid, boric acid and their derivatives and salts; chelating acids such as EDTA, as well as other acids that are commonly used for chromatographic sample prep and known to those of skill in the art.

In some embodiments, the aqueous solution includes a base. Examples of bases that can be used include inorganic bases such as sodium hydroxide, potassium hydroxide; ammonium hydroxide and its derivatives and salts, alkyl amines such as methylamine, ethylamine, triethylamine; pyridine, pyrrolidine and their salts, as well as other bases that are commonly used for chromatographic sample prep and known to those of skill in the art. Acids, bases, and their salts are commonly added to samples to improve the analyte solubility by changing the solution pH. Sometimes these additives can further stabilize the analytes by forming ion pairs.

The method 100 also includes placing the solution in contact with a polypropylene substrate having a deactivated surface 110. The deactivated surface reduces adsorption of the hydrophobic molecule relative to a polypropylene substrate that has not been deactivated. The deactivated surface can be more hydrophilic (or less hydrophobic) than the polypropylene substrate without a deactivated surface. The hydrophobicity or hydrophilicity of the surface can be measured using techniques known to those of skill in the art, for example, by determining the average water contact angle on the substrate. Generally, if the water contact angle is less than 90°, the substrate surface is considered hydrophilic and if the water contact angle is greater than 90° then the substrate surface is considered hydrophobic. The deactivated surface can have a water contact angle that is less than the water contact angle of the polypropylene substrate without a deactivated surface. In some embodiments, the deactivated surface has a water contact angle that is one or two degrees less than the water contact angle of the polypropylene substrate without a deactivated surface. In other embodiments, the deactivated surface has a water contact angle that is more than two degrees less than the water contact angle of the polypropylene substrate without a deactivated surface, for example 3, 4, 5, 6, 7, 8, 9, or 10 degrees less than the water contact angle of the polypropylene substrate without the deactivated surface.

There are numerous ways to treat a surface to deactivate it. For example, various surface treatment approaches can be categorized into the two following principles: (1) attaching hydrophilic molecules on the surface by (a) using physical or chemical vapor deposition (PVD or CVD), (b) using wet synthetic chemistry methods such as derivatization or grafting to form new chemical bonds, or (c) layering or coating the hydrophilic molecules on the surface such as by forming self-assembled layers or by creating aggregates; and (2) changing the surface properties by altering the surface molecular structure and/or surface finish by (a) chemical etching, (b) forming nanostructures, or (c) plasma treatment. A polypropylene substrate can be deactivated by a plasma. For example, the polypropylene substrate can be treated with a high energy plasma. The polypropylene surface can be treated with oxygen plasma and water vapor.

In some embodiments, a deactivated surface is a surface that has been chemically altered without a deposition applied to alter its surfaces (e.g., chemically altered without a coating). Some substrates, vials, tubes and plates of interest are formed at least in part of polypropylene having a surface that is not coated (i.e., uncoated surface) but is modified to deactivate it—to reduce its hydrophobicity. For example, a substantially polypropylene substrate can be exposed to a plasma to chemically alter its surface (i.e., no coating applied or deposited).

In other instances, the hydrophilic nature of a surface can be enhanced with a coating or film deposit. For example, EP patent publication number EP 2 532 716 describes several coating techniques or methods used to minimize adsorption of protein. In particular, an added silicon coating to a reaction vessel is described as minimizing protein adsorption from a sample. In addition, methods involving hydrophilic polymer coatings (e.g., U.S. Pat. No. 6,765,069), methods involving the plasma deposition of an oligomeric ethylene glycol derivative (DE 195 48 152), and methods involving coating of an organic compound or monomer by gas or plasma polymerization (U.S. Pat. No. 6,482,531) are described as having a low affinity for protein.

The method 100 also includes analyzing the sample 115. For example, the sample can be analyzed with mass spectrometry, quantum dots analysis, or fluorescence. In some embodiments, the sample can be analyzed with one or more of the following detectors: UV (ultra-violet), VIS (visible), PDA (photodiode array), TUV (tunable UV), RI (refractive index), IR (infrared), RAMAN, Conductivity, Evaporative Light Scattering Detection, Multi-angle light scattering detectors (MALLS), light scattering detectors, charge detectors, particle counters, mei-scattering detectors, charged aerosol detector, FID (flame ionization detector), pulsed electrochemical detection, thermal conductivity detector, optical rotation detector, electrochemical detector, deflection detector, chemiluminescence nitrogen detector, NMR (nuclear magnetic resonance), Coulometry, titration, viscosity, and calorimetry. In some embodiments, the sample can be analyzed using electrochemical techniques or light-scattering techniques.

The deactivated surface can be a vial or a plate. For example, a vial can have a deactivated surface. The vial can be used to store the sample. The plate can be, for example, a 96 well plate that is used in laboratories for testing. In some embodiments, the plate or vial with a deactivated surface is uncoated.

In some embodiment, the method 100 also includes separating the sample 120. The sample can be separated with chromatography, for example liquid chromatography.

The method 100 can have between about 75% to about 100% recovery. For example, the method can have about 75%, 80%, 85%, 90%, 95%, or 100% recovery.

Factors Influencing Recovery

Peptide solution standards in the concentration range of 20 pg/mL to 100 ng/mL were prepared in various sample matrices and stored in several commercially available sample containers prior to LC-MS analysis. To accurately determine the recovery of challenging peptides, solutions containing carrier proteins were used as recovery reference solutions: the solutions were prepared in groups, with and without 0.1% rat plasma, and the peptide recovery was calculated by comparing the peptide peak area from the solution that did not contain the blocking agent to the reference peak area. Peptides in each sample were separated using a 2.1×50 mm, 1.6 µm charged surface solid core $C_{18}$ column (CORTECS® C18+ column, commercially available from Waters Technologies Corporation, Milford, Mass.) on a low dispersion LC system (ACQUITY® I-Class System, commercially available from Waters Technologies Corporation, Milford, Mass.) with a water-acetonitrile linear gradient, each with 0.1% formic acid, and detected using a tandem quadrupole MS (XEVO® TQ-S, commercially available from Waters Technologies Corporation, Milford, Mass.) in the selective reaction monitoring (SRM) mode. To understand the role of the container's surface properties on peptide recovery, polypropylene vials and 96-well plates, deactivated polypropylene vials and plates (in accordance with the present technology), and commercially available plates designed for protein applications were evaluated. Other experimental conditions, such as the composition of the peptide sample and peptide concentration, were varied to highlight how these factors affected peptide recovery.

Polypropylene sample containers are commonly used for various LC-MS applications because of their good chemical compatibility and a wide selection of shapes and sizes. Polypropylene 96-well plates have been particularly popular in high-throughput applications with the availability of multichannel pipettes and robots. Another reason they are used frequently with protein or peptide samples is that they are less likely to induce analyte loss from ionic attractions than glass containers. Any analyte lost on the polypropylene containers, when it occurs, is likely a result of hydrophobic interactions.

Type of Container—Glass or Plastic

Figure 3:
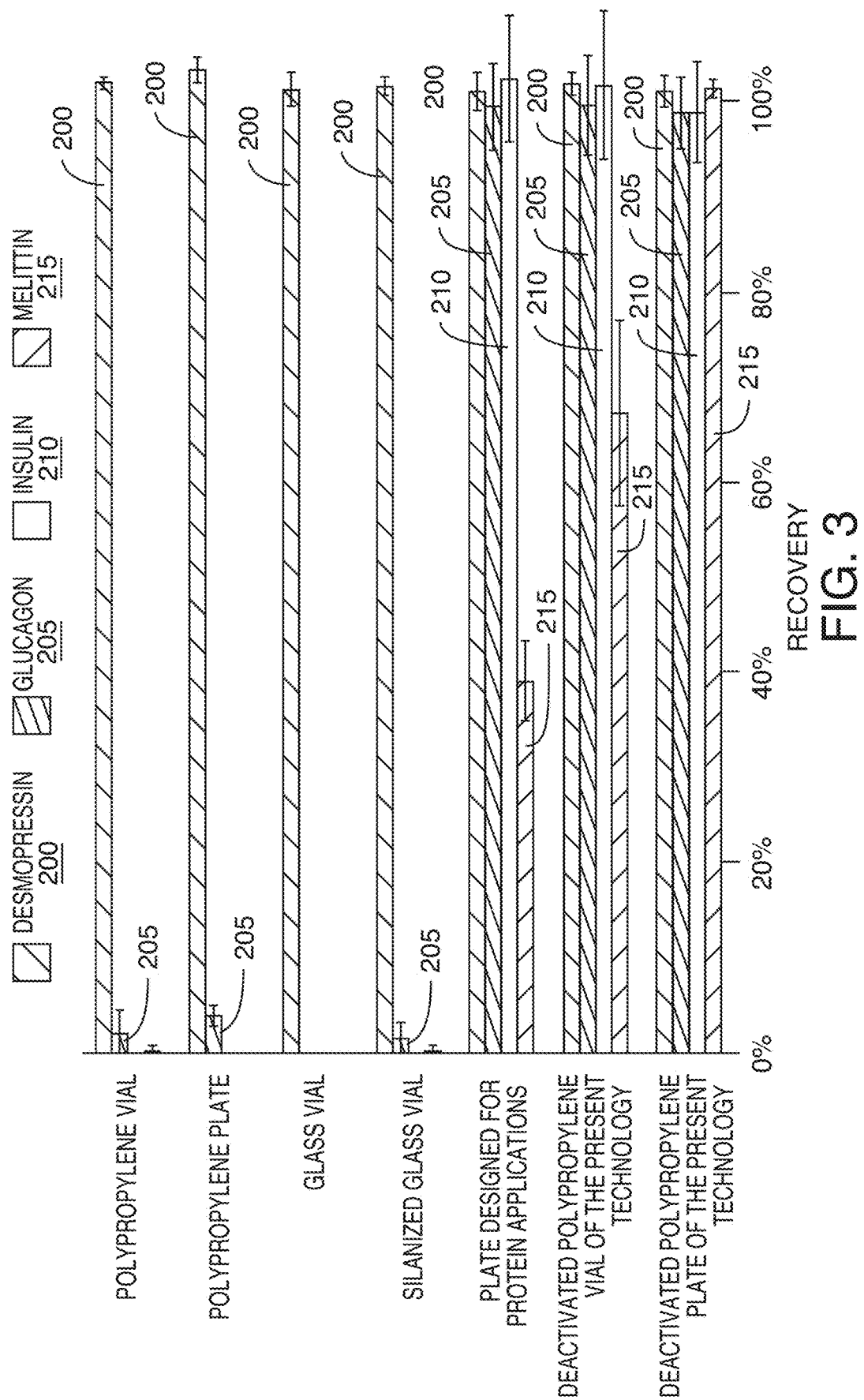
FIG. 3 is a graph showing the average recovery (n=4) of four peptides (1 ng/mL per peptide) after 24 hours of storage at 4° C., according to an illustrative embodiment of the technology. The error bars show the standard deviations. Peptide solutions were prepared in 80:20 water:acetonitrile solution which was acidified with 0.2% trifluoroacetic acid (TFA).

FIG. 3 compares the recovery of four peptides that were prepared in a typical LC-MS diluent and stored in various sample containers. The recoveries of the peptides correlated well with their relative hydrophobicity. The least hydrophobic peptides produced the highest recovery values while the most hydrophobic peptides showed the lowest recovery values. All containers showed complete recovery of desmopres sin 200, the least hydrophobic peptide (MW 1069, HPLC index 16.8). Polypropylene containers, glass, and deactivated (silanized) glass showed little or no recovery for three hydrophobic peptides, glucagon 205 (MW 3482, HPLC index 86), bovine insulin 210 (MW 5734, HPLC index>120), and melittin 215 (MW 2846, HPLC index 124.4). Of the three peptides, melittin 215 showed the most drastic recovery difference among the tested containers. A commercially available plate for protein applications showed higher recovery than the polypropylene and glass surfaces but with some mixed results. From the results shown, the loss of peptides in the polypropylene containers depended on their relative hydrophobicity. The loss of peptides in the polypropylene containers depends on their relative hydrophobicity and the losses can be further mitigated by regulating the strength of the hydrophobic interactions. Next how much recovery is influenced by the elution strength of the sample matrix is examined.

Sample Matrix—Organic Solvent Content

Figure 4A:
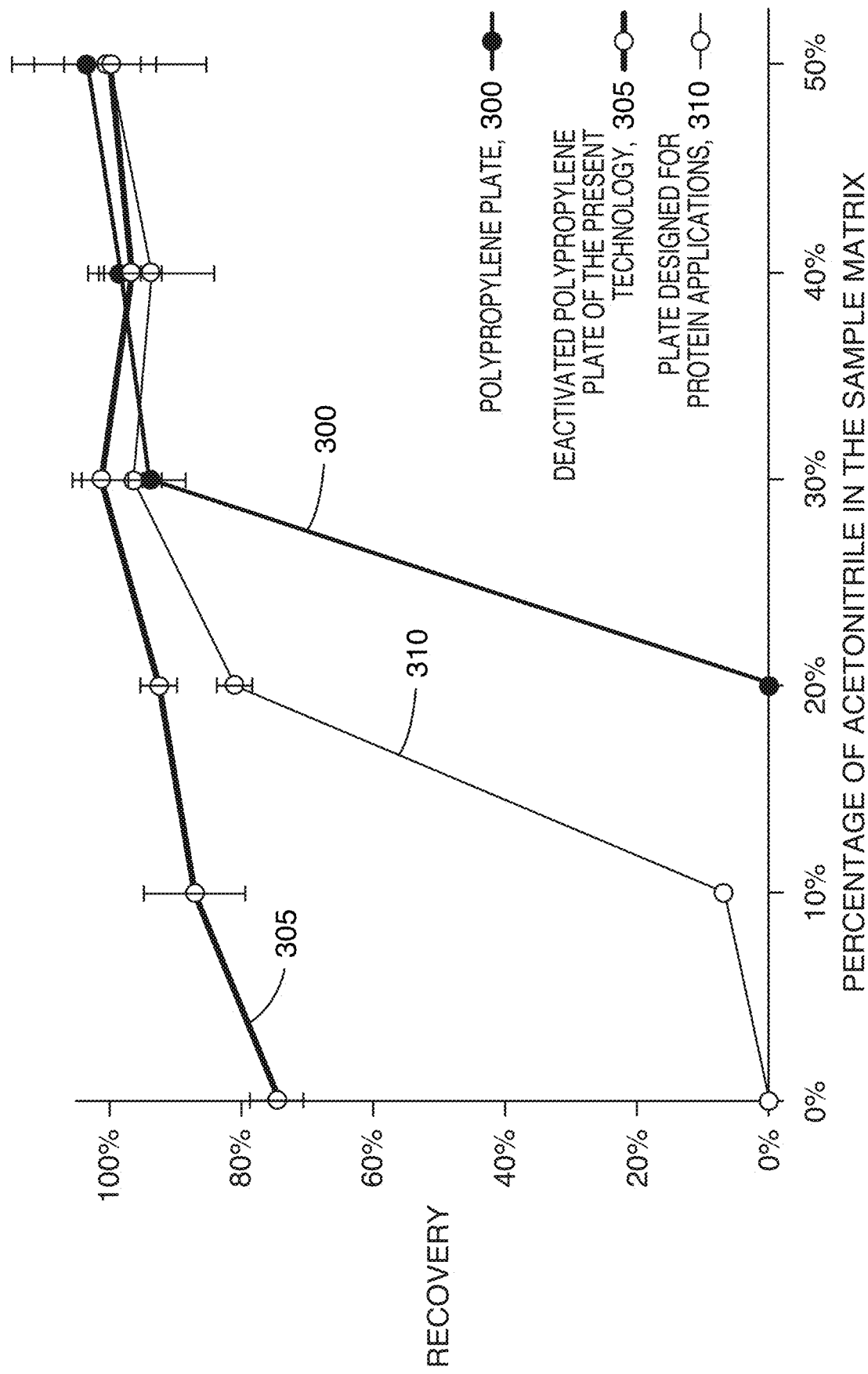
FIG. 4A is a graph showing the average recovery (n=4) of 1 ng/mL teriparatide after 24 hours of storage at 4° C., according to an illustrative embodiment of the technology. The error bars show the standard deviations. The peptide solutions were prepared in various water/acetonitrile mixtures and acidified with 0.2% TFA. After 24 hours of storage, the samples were diluted with appropriate water/acetonitrile content to 20% before injection. The teriparatide peak quantitation, and thus the recovery calculation were not compromised by poor retention.

FIG. 4A shows the recovery of teriparatide, another hydrophobic peptide (MW 4118, HPLC index 90.4), in sample matrices with varied acetonitrile content. In general, recoveries improved as the sample matrix contained more acetonitrile, while the minimum acetonitrile concentration that led to full recovery was not the same for different sample containers (polypropylene plate 300, deactivation polypropylene plate 305, and plate designed for protein applications 310). Using highly organic sample matrix appeared to be the easiest and the most effective way to completely recover hydrophobic peptides. Teriparatide solutions prepared with 30% or more acetonitrile can be stored in any of the three containers without the risk of analyte loss. While quite effective, this approach doesn't always work. For LC-MS, analytes in samples prepared in highly organic injection solutions may not retain well on the chromatographic column.

Figure 4B:
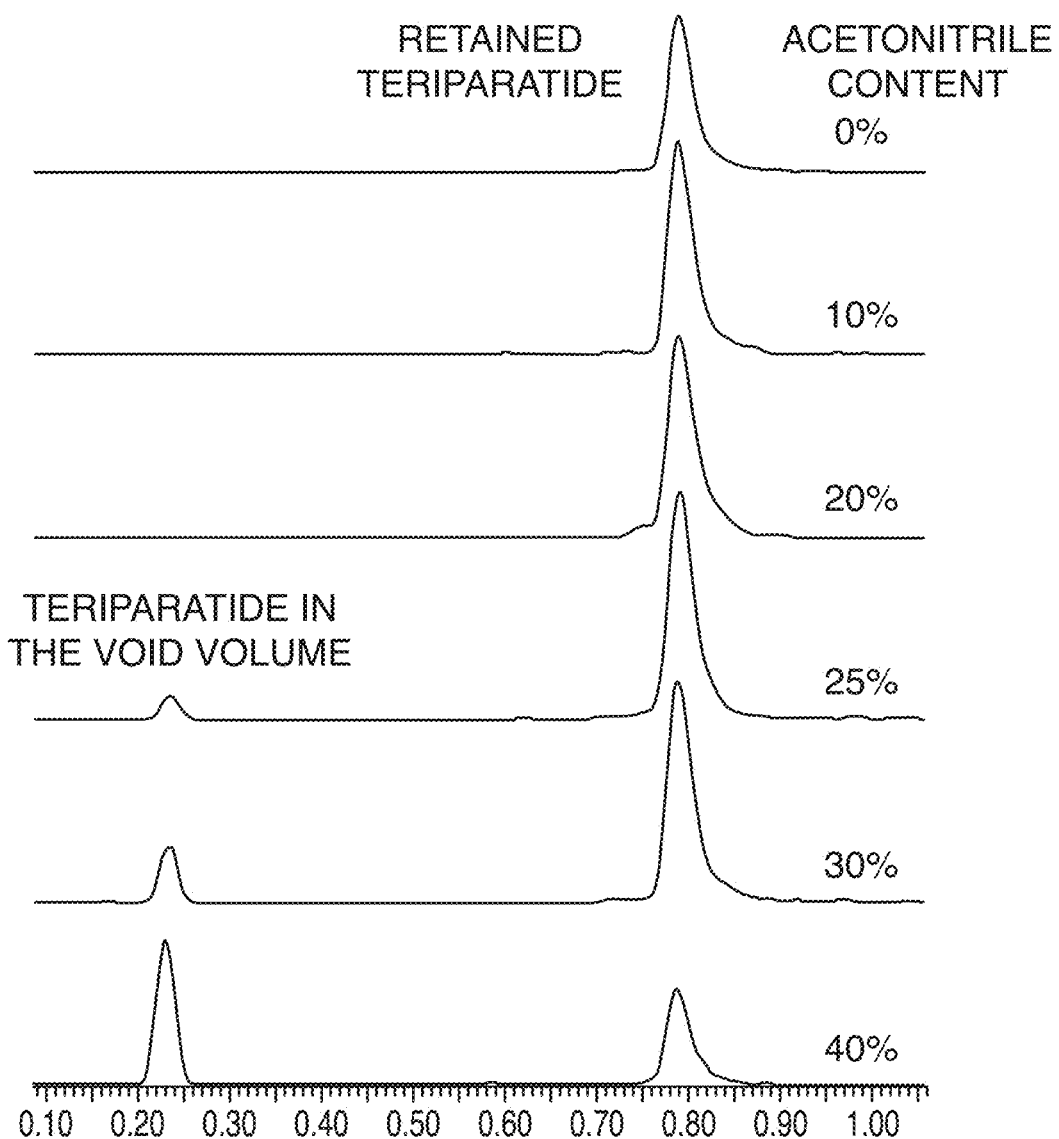
FIG. 4B are chromatograms of teriparatide, according to an illustrative embodiment of the technology. Teriparatide samples were prepared in sample matrices with varied water/acetonitrile ratios, and were injected without dilution.

FIG. 4B shows the disrupted retention of teriparatide as the acetonitrile concentration in the sample matrix was increased. When the acetonitrile percentage in the sample matrix was equal to or greater than 20%, teriparatide breakthrough peaks were observed in the void volume. It was thus necessary to prepare teriparatide samples with less than 25% acetonitrile to achieve good chromatography. However, limiting the concentration of acetonitrile to less than 25% with the polypropylene plate or the plate designed for protein applications cause teriparatide to be lost on the container surface (see, FIG. 4A). The same sample can be stored in a plate with the deactivated surface designed for minimizing hydrophobic nonspecific adsorption without the risk of analyte loss.

To achieve a teriparatide recovery greater than 90% one much prepare the solution with more than 30% acetonitrile with using a polypropylene plate (that has not been deactivated according to the present technology), and more than 25% acetonitrile is using a commercially available low bind plate. However, using a deactivated polypropylene plate of the present technology, the sample solution can be made with as little as 10% acetonitrile while still achieving greater than 90% recovery. Only the samples prepared in a deactivated polypropylene plate achieved the maximum recovery without impacting the downstream LC-MS analysis.

Sample Matrix—Acidic/Basic Additive and pH

Figure 5:
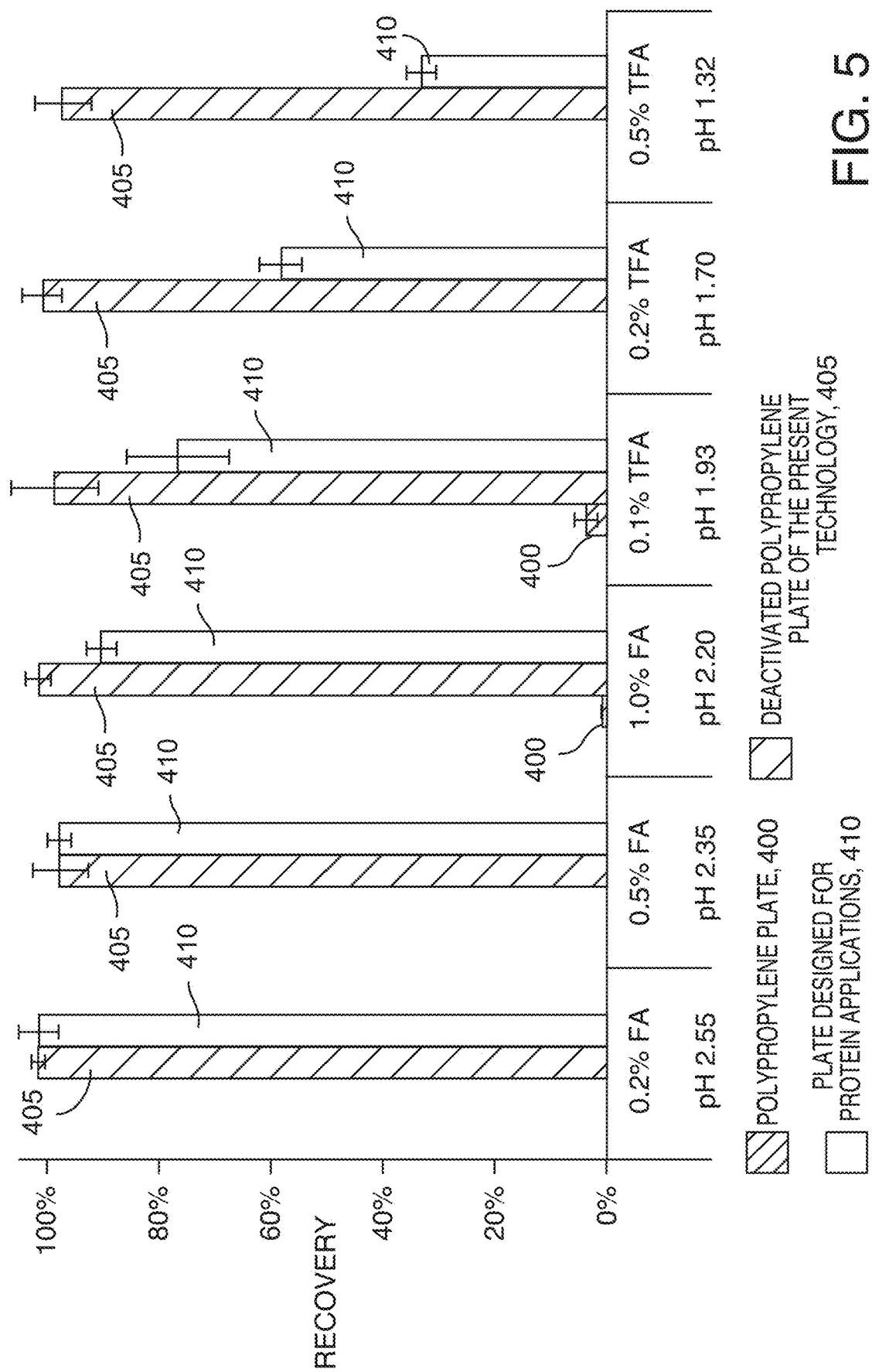
FIG. 5 is a graph showing average recovery (n=4) of 1 ng/mL melittin after 75 hours of storage at 10° C., according to an illustrative embodiment of the technology. The error bars show the standard deviation. The peptide solutions were prepared in an 80:20 water:acetonitrile mixture and acidified with formic acid (FA) or trifluoroacetic acid (TFA) while varying the volume (v/v). The pH of the solutions were experimentally measured.

The choice of the acidic additive of the pH in the sample matrix also affects the peptide recovery. FIG. 5 shows the recovery of melittin after 75 hours of storage. Using a weak acid such as formic acid at a low concentration helped increase the melittin recovery, but the increase was not as drastic as changing the acetonitrile concentration in the sample matrix. Melittin was never recovered from the polypropylene plate 400 by changing the additive only (the recovery for the polypropylene plate 400 was zero where no corresponding bars on the graph are reflected, for example, the recovery for the polypropylene plate 400 was zero for 0.2% FA at pH 2.55, 0.5% FA at pH 2.35, 0.2% TFA at pH 1.70 and 0.5% TFA at pH 1.32), whereas it was completely recovered from the deactivated polypropylene plates 405 of the present technology, which are designed for minimizing hydrophobic nonspecific adsorption regardless of the additive type and concentration. Plates designed for protein applications 410, were also studied. When using a plate that may have an intermediate surface binding activity, the recovery using various additives in different concentrations can be monitored. It should be noted that the choice of the acidic additives has an influence on the peak shape in the downstream LC-MS analyses, although the effect was not as drastic as the additives in the mobile phase. Formic acid in the sample, being a volatile additive, gave a stronger MS signal but led to poor chromatographic peak shapes compared to trifluoroacetic acid.

Factors such as sample volume and storage time also influence the peptide recovery. In general, the smaller the sample volume and the longer the sample is stored in a container, the poorer the recovery. In practice, however, these factors can be difficult to control. For example, the length of time a sample spends in storage is often dictated by instrument availability, the number of samples in the queue, and the LC-MS run time. On the other hand, sample volume is limited by sample availability and sample prep protocol.

Figure 6:
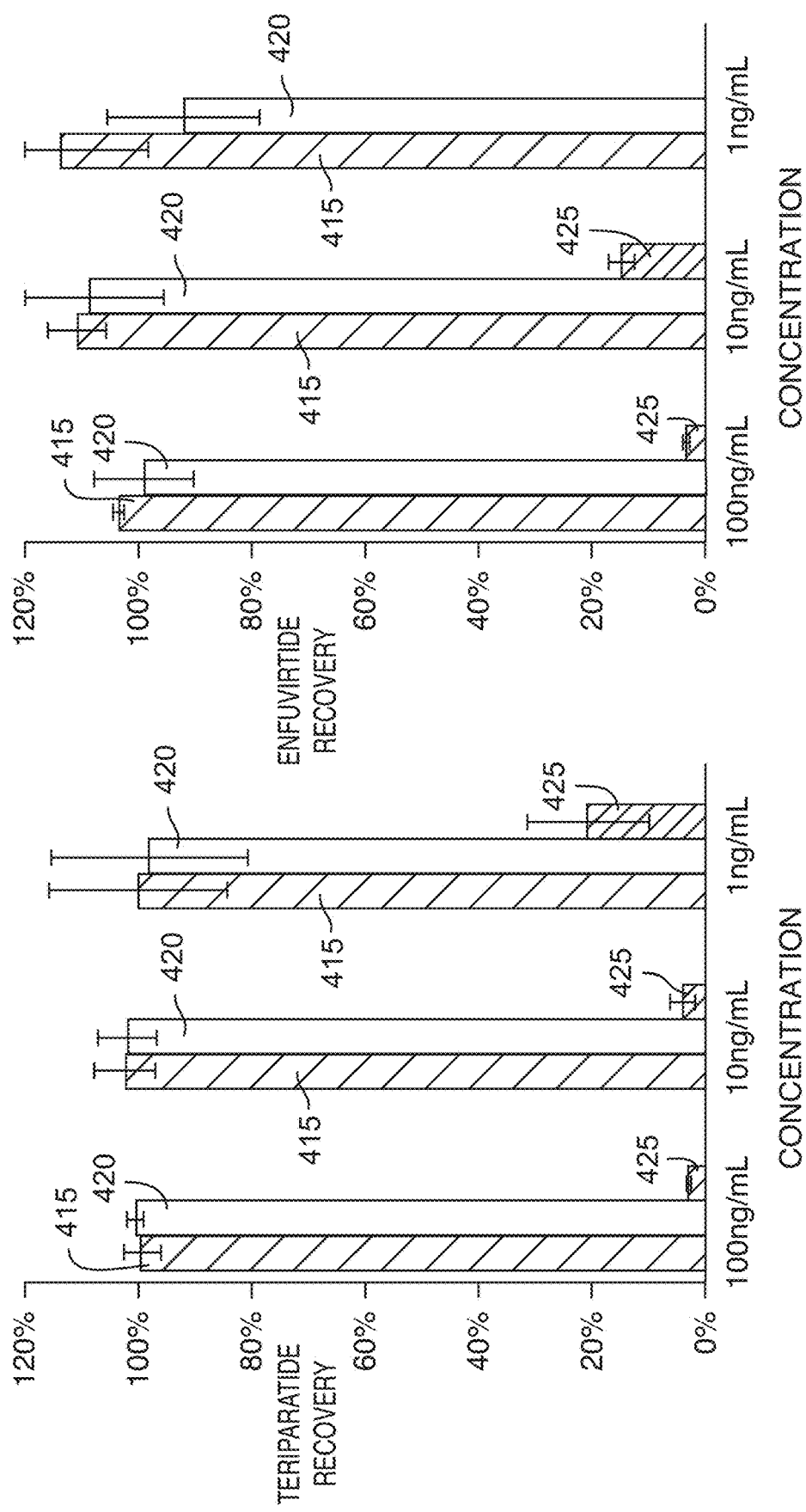
FIG. 6A is a graph showing the average recovery (n=3) of teriparatide at various sample concentrations after 24 hours of storage at 10° C., according to an illustrative embodiment of the technology. The error bars show the standard deviations. The peptide solutions were prepared in an 80:20 water:acetonitrile mixture with 2% ammonium hydroxide. The pH of the solutions was 11.5 from the direct measurement. Note the increased measurement variability at lower sample concentrations (greater error bars), which also affected the accuracy of recovery from the polypropylene plate.
FIG. 6B is a graph showing the average recovery (n=3) of enfuvirtide at various sample concentrations after 24 hours of storage at 10° C., according to an illustrative embodiment of the technology. The error bars show the standard deviations. The peptide solutions were prepared in an 80:20 water:acetonitrile mixture with 2% ammonium hydroxide. The pH of the solutions was 11.5 from the direct measurement. Note the increased measurement variability at lower sample concentrations (greater error bars), which also affected the accuracy of recovery from the polypropylene plate.

The choice of sample additives is not limited to acids. Bases can also be used to increase solubility or to achieve better downstream chromatography. Changing pH is also a versatile tool for controlling the analyte chemical properties to promote or prevent both ionic and hydrophobic interactions. Deactivated polypropylene plates can be used for storing basic samples solutions as well as acidic sample solutions. FIGS. 6A and 6B show the average recovery (n=3) of two hydrophobic peptides, teriparatide and enfuvirtide (MW 4492, HPLC index 155.9) in basic sample solutions (pH 11.5) containing 2% ammonium hydroxide. The two hydrophobic peptides were completely recovered from the deactivated polypropylene plates 415 while they were almost totally lost when the sample was stored in a polypropylene plate 425. Results from a commercially available low bind plate 420 are also shown.

Figure 7:
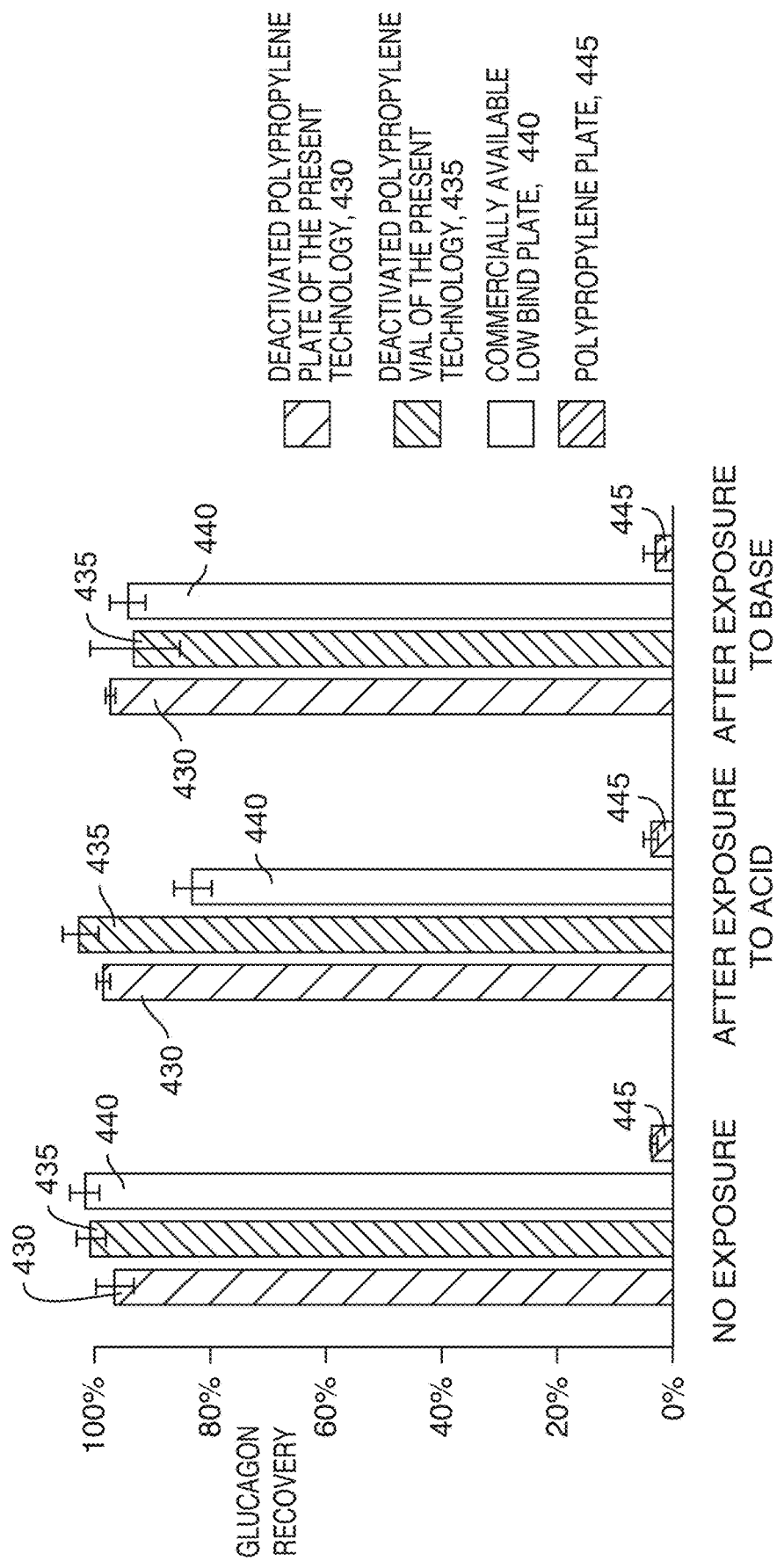
FIG. 7 is a graph showing the average recovery (n=3) of 1 ng/mL glucagon after 20 hours of storage at 4° C., in sample containers previously exposed to a strong acid or base, according to an illustrative embodiment of the technology. The error bars show the standard deviations. Tested sample containers were first filled with 1 M nitric acid or 1 M sodium hydroxide solutions (pH 0 and 14, respectively) and sealed with appropriate caps to prevent evaporation. After 24 hours, the containers were emptied and thoroughly rinsed with DI water 3 times while aspirating the water up and down during the rinses to facilitate mass transfer in the containers. Recoveries of 1 ng/mL glucagon were measured after 20 hours of storage at 4° C. using the vials and plates that were exposed to the acid and base and then rinsed, as well as using reference vials and plates that were not exposed to the acid or base (no exposure). The glucagon solutions were prepared in an 80:20 water/acetonitrile mixture with 0.2% TFA.

FIG. 7 shows another example of using the deactivated polypropylene plates in extreme pH conditions. Occasionally sample plates and vials are exposed not just to moderately acidic or basic solutions but to extremely caustic solutions which can damage the surface and modify its properties. To investigate the effect of extreme acids or bases on the surfaces, sample containers were exposed to 1 M nitric acid or 1 M sodium hydroxide (pH 0 and 14, respectively) for 24 hours prior to measuring peptide recoveries. Both the deactivated polypropylene plates and vials showed no change in glucagon recoveries after the exposure to either strong acid or base while the other low bind plate showed a decreased recovery after exposing it to 1 M nitric acid.

The pH of the sample matrix and the choice of additives are variables that influence peptide recoveries, but the selections can be limited according to the experimental conditions, for example, upstream and/or downstream workflows and analyte stability. Using the deactivated polypropylene plates and vials of the present technology, which offer maximum recoveries over a wide range of experimental conditions, makes it easier to select an optimal sample matrix condition that is compatible with the rest of the workflow while maintaining the analyte stability and recovery, in comparison with a sample container that may be used for only limited conditions.

Peptide Concentration

Figure 8:
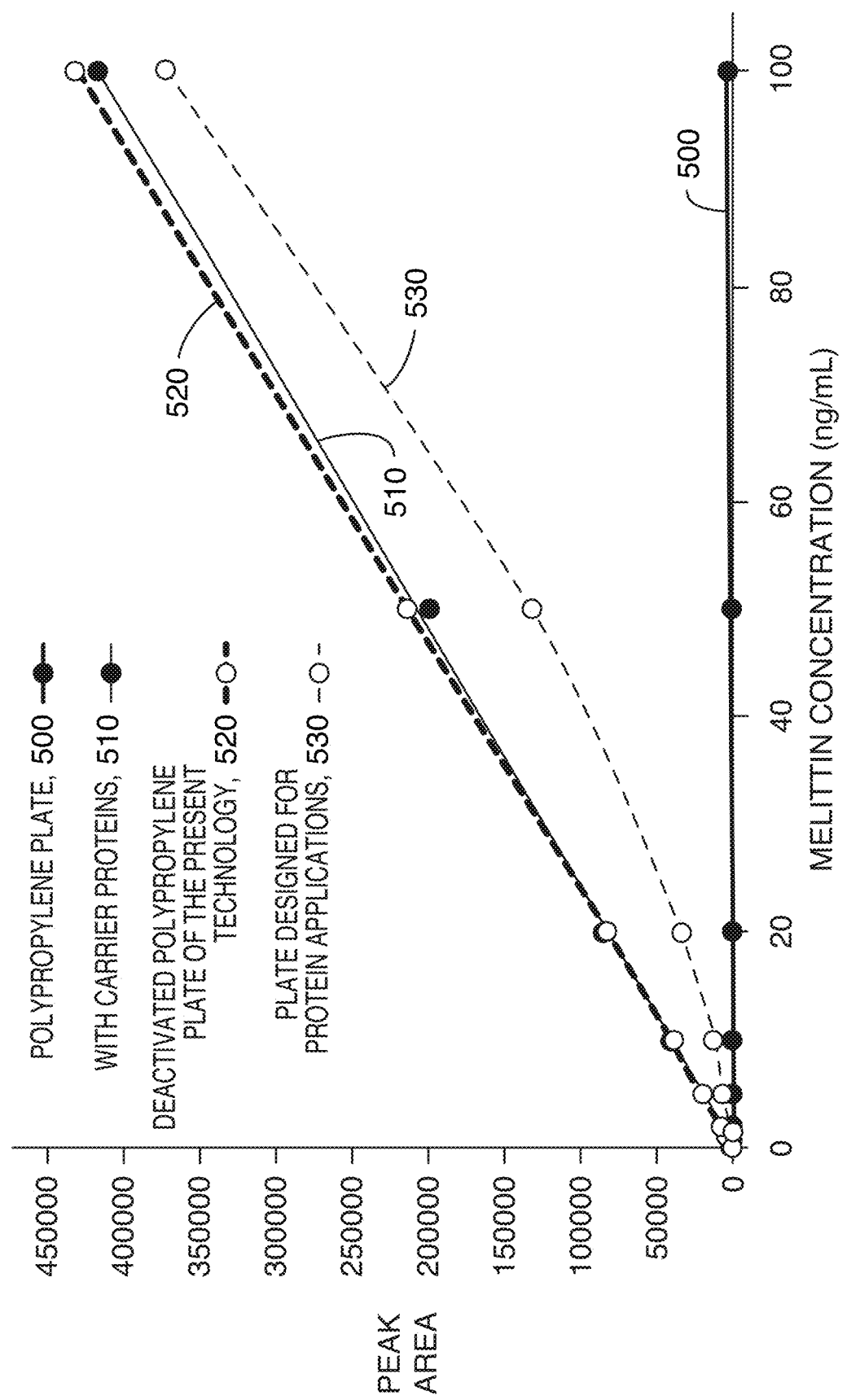
FIG. 8 is a graph showing calibration curves for melittin in the concentration range of 20 pg/mL to 100 ng/mL, according to an illustrative embodiment of the technology. The calibration standards were prepared with 80:20 water: acetonitrile and 0.2% TFA in each sample container by serial dilution. To obtain the 'true' calibration curve without suffering from the analyte loss, one set of calibration standards was prepared with 0.1% rat plasma as carrier proteins. All other standards were prepared without carrier proteins.

Peptide concentration is another variable that affects recovery but cannot be independently controlled. It is particularly problematic when constructing a calibration curve. FIG. 8 shows calibrations curves for melittin using various sample containers (polypropylene plate 500, the deactivated polypropylene plates 520, and plate designed for protein applications 530). To illustrate the ideal calibration curve that was not affected by the peptide loss, one sample set was prepared with 0.1% rat plasma as carrier proteins 510. Peptide loss can be easily identified from the shape of the calibration curve. Linear calibration curves were obtained when no peptide loss occurred on the sample container. However, in some cases, the peptide loss was so severe that the calibration curve could not be construed at all. Even when peptide loss was not so severe, it was impossible to construct a calibration curve: the trace formed a concave curve of which the curvature depended loosely on the severity of the peptide loss. This curve showed the nonlinear relationship between the peptide loss and the concentration and would not fit a linear model.

Analyte loss in sample containers is a significant problem in peptide quantitation. Failure to mitigate it can lead to hours of wasted time during method development, or even worse, to suboptimal methods that are limited by poor sensitivity and reproducibility. The most effective way to reduce the loss of hydrophobic peptides was to change the organic solvent content of the sample. However, there were limits to this approach. When the organic solvent content was above a certain level there was an increased risk of poor chromatography, while below a certain level there was an increased risk of low recovery. The types and concentrations of acidic additive in the sample matrix also influence peptide recovery. Using a container (e.g., a vial and/or plate) with a low surface binding property (e.g., a deactivated surface) protects against peptide loss and is an LC-MS friendly. It simplifies the process of selecting storage conditions without compromising peptide recovery.

Storage Time and Temperature

Figure 9:
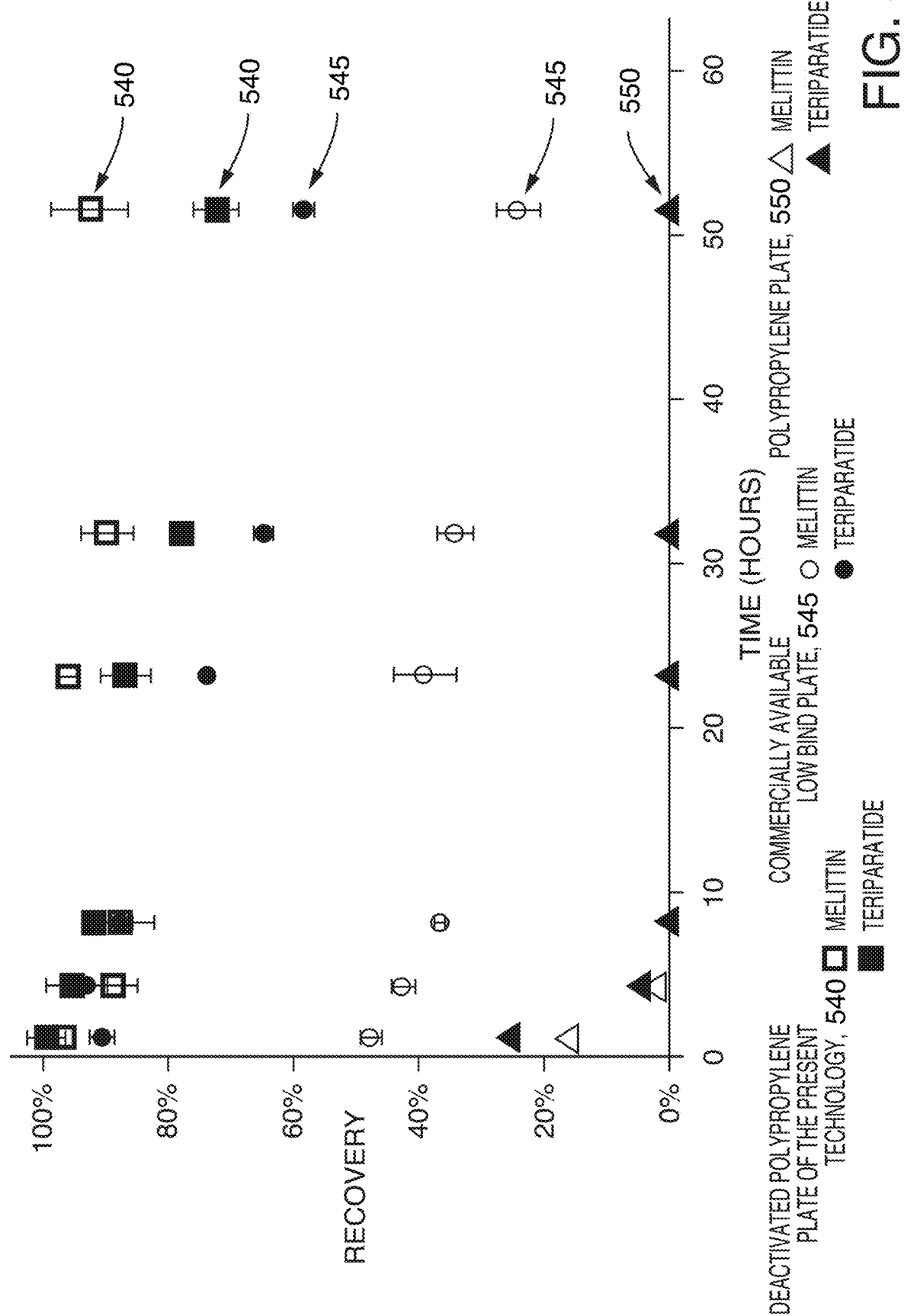
FIG. 9 is a graph showing average recovery (n=4) of 1 ng/mL teriparatide (closed circles) and melittin (open circles) over 51 hours of storage at 10° C., according to an illustrative embodiment of the technology. The error bars show the standard deviations. The peptide solutions were prepared in an 80:20 water/acetonitrile mixture and acidified with 0.2% TFA.

FIG. 9 shows the recoveries of 1 ng/mL melittin and teriparatide stored in various sample containers, monitored over 51 hours. From above, we know that melittin and teriparatide stored in a polypropylene plate would be completely lost in 24 hours. If we follow their recoveries over time, the recoveries were about 20% after 1 hour and dropped to almost zero after 8 hours. Peptides stored in other containers followed a similar pattern, where their recoveries are gradually decreased over time but at different rates depending on the peptides and containers. In general, peptides stored in a deactivated polypropylene plate 540 were much better recovered than peptides in other containers, i.e., commercially available low bind plates 545 and polypropylene plates 550. Both melittin and teriparatide showed increased loss over time but followed different trends. Most notable from the data using the commercially available low bind plate 545, a significant amount of melittin was lost within the first hour while the losses during the following hours were not as quick. On the other hand, teriparatide showed a consistent rate of loss over time. A similar but much subtler pattern could be noted from the data using the deactivated polypropylene plate 540, where the recovery of teriparatide decreased over time while melittin recovery changed little. Without being bound to theory, it is speculated that this is due to the difference in adsorption kinetics for melittin and teriparatide. Regardless of the difference in kinetics, deactivated polypropylene plate offered better recovery than other containers even after extended storage.

Recovery of analytes over time can be referred to as stability. For example, a direct-to-MS analysis (as opposed to a sample sent through a liquid chromatography column prior to MS analysis) of a sample from a deactivated polypropylene plate would have approximately the sample result irrespective of the amount of time to sample was in contact with the deactivated polypropylene plate (see FIG. 9). In some embodiments, the sample can be in contact with the deactivated polypropylene plate for more than a day, more than two days, more than three days, or longer, for example, more than a month or more than two months without having a detrimental impact of the recovery of the analyte.

Figure 10:
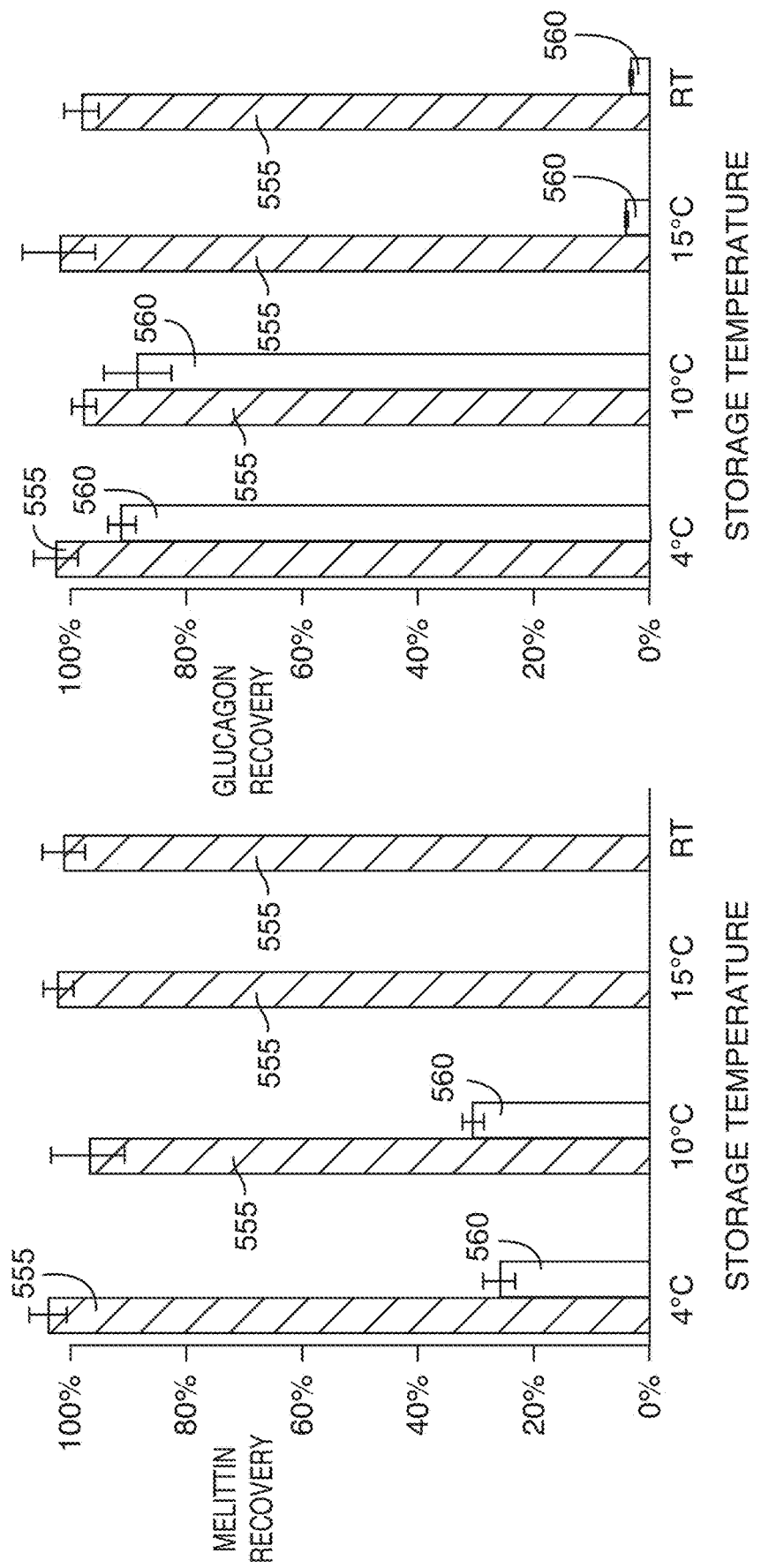
FIG. 10A is a graph showing average recovery (n=4) of 1 ng/mL melittin (solid bars) after 47 hours of storage at different temperatures, according to an illustrative embodiment of the technology. The error bars show the standard deviations. The peptide solutions were prepared in an 80:20 water/acetonitrile mixture and acidified with 0.2% TFA. Room temperature (RT) was approximately 25° C.
FIG. 10B is a graph showing average recovery (n=4) of 1 ng/mL glucagon (checked bars) after 47 hours of storage at different temperatures, according to an illustrative embodiment of the technology. The error bars show the standard deviations. The peptide solutions were prepared in an 80:20 water/acetonitrile mixture and acidified with 0.2% TFA. Room temperature (RT) was approximately 25° C.

Another important factor that influences the kinetics of nonspecific binding is temperature. In kinetic theory, temperature influences many reactions by promoting molecular movement and/or supplying energy. FIGS. 10A and 10B show the effect of sample storage temperature on the recovery of melittin and glucagon after 47 hours. It is remarkable that highly hydrophobic melittin can be completely recovered from deactivated polypropylene plate 555 stored at various temperatures including room temperature (~25° C.). It is however not recommended to store samples at room temperature because of other concerns such as sample degradation. Melittin stored in commercially available low bind plates 560 was mostly lost. About 25% was recovered if stored at or below 10° C. while complete loss was observed if stored above 10° C. To confirm whether the abrupt transition in recovery at approximately 15° C. was true, the recovery of glucagon, a less hydrophobic peptide, was examined. While the recoveries were in general greater than those for melittin, the same abrupt transition in recovery was observed. Because the same peptides were completely recovered from the deactivated polypropylene plate at temperatures over 15° C., we can conclude that the losses observed from the other low bind plate are due to NSB rather than peptide degradation. This result is another example demonstrating that peptide adsorption on deactivated polypropylene plates and vials is a slower and less favorable process compared to similar adsorption on other containers, making it more compelling to choose deactivated polypropylene plates and vials for working with sticky analytes.

Sample Volume

Figure 11:
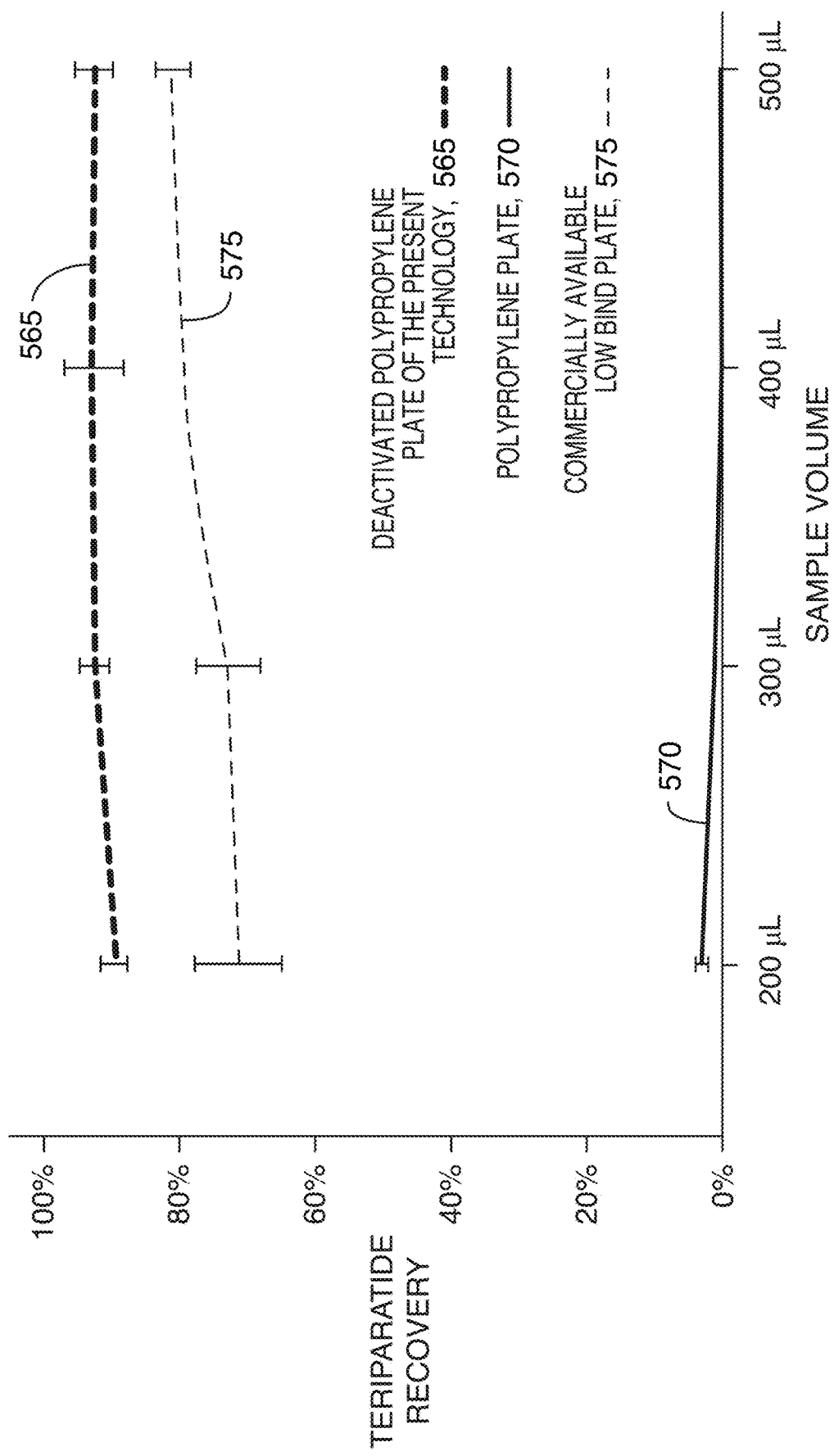
FIG. 11 is a graph showing average recovery (n=4) of 1 ng/mL teriparatide after 24 hours of storage at 4° C., according to an illustrative embodiment of the technology. The error bars show the standard deviations. The peptide solutions were prepared in an 80:20 water/acetonitrile mixture and acidified with 0.2% TFA.

In typical chemical reactions, the difference in volume is seldom an important factor that influences the kinetics. For surface adsorption on a sample container, however, sample volume does influence NSB because the exposed surface area is changed. For most sample containers, the surface-to-volume ratio increases as sample volume decreases, and consequently more NSB is observed. This is particularly undesirable in challenging LC-MS analyses where samples are limited in volume and analyte concentrations are low. FIG. 11 shows the effect of sample volume on peptide recoveries. Teriparatide stored in a commercially available low bind plate 575 showed decreased recovery and increased variability as the sample volume is decreased. On the other hand, teriparatide stored in a deactivated polypropylene plate 565 was completely recovered regardless of the sample volume, without showing increased variability at low concentrations. Teriparatide stored in a polypropylene plate 570 showed almost no recovery.

Sealing

Figure 12A:
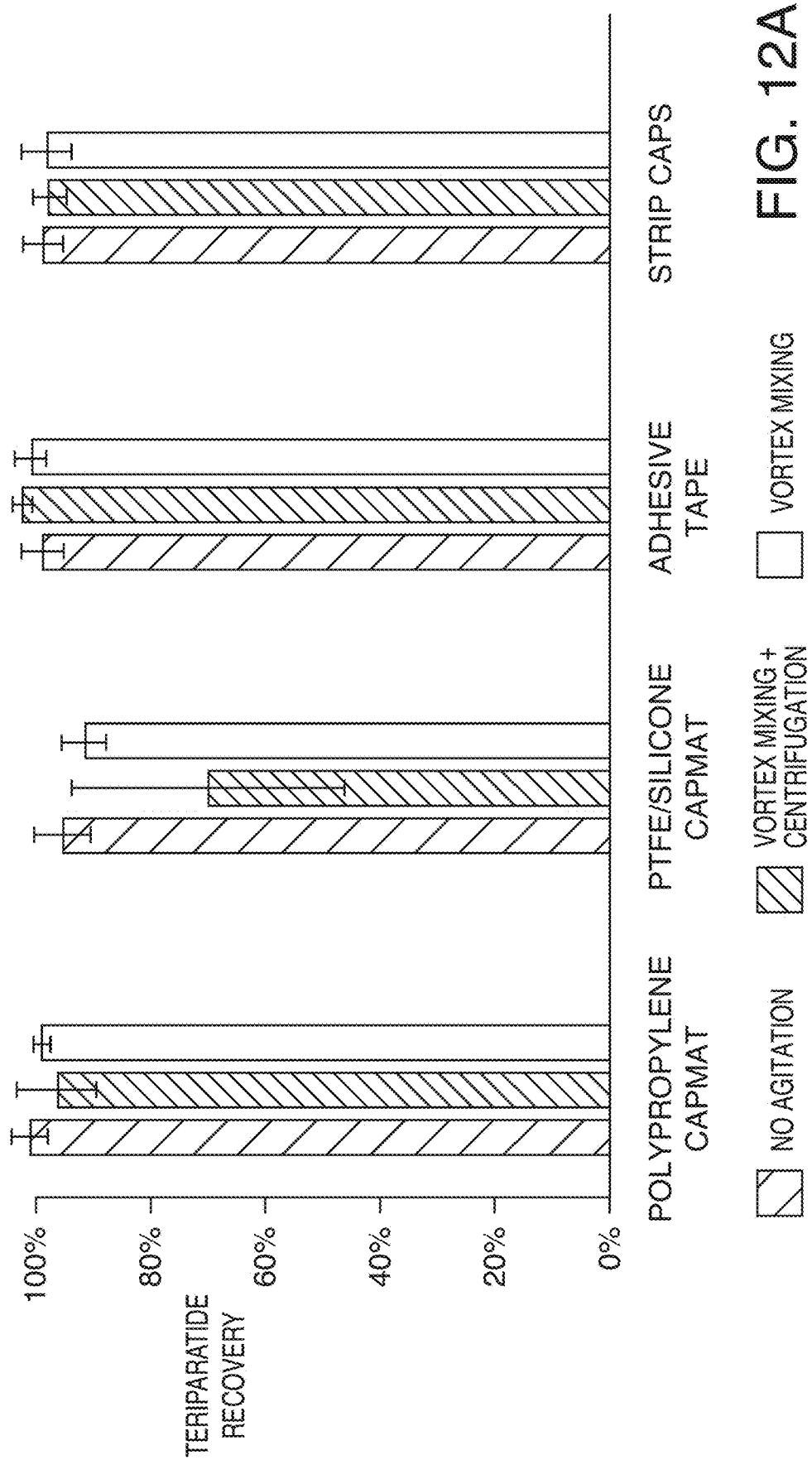
FIG. 12A, is a graph showing average recovery (n=4) of 1 ng/mL teriparatide in deactivated polypropylene plates capped with various sealing options and physical agitations, according an illustrative embodiment of the technology. The plates were stored at 10° C. for 22 hours before LC-MS analyses. The error bars show the standard deviations. The peptide solutions were prepared in an 80:20 water/acetonitrile mixture and acidified with 0.2% TFA. Tested caps were: 1) a polypropylene cap mat, 2) a PTFE/silicone cap mat, 3) adhesive tape seal, and 4) a strip plug cap. After capping the plates, one plate was left undisturbed; the second plate was agitated by vortex mixing for 5 min and centrifuged at 4000 rpm for 1 min to bring down the solution to the wells, and the third plate was agitated by vortex mixing for 5 min only.
Figure 12B:
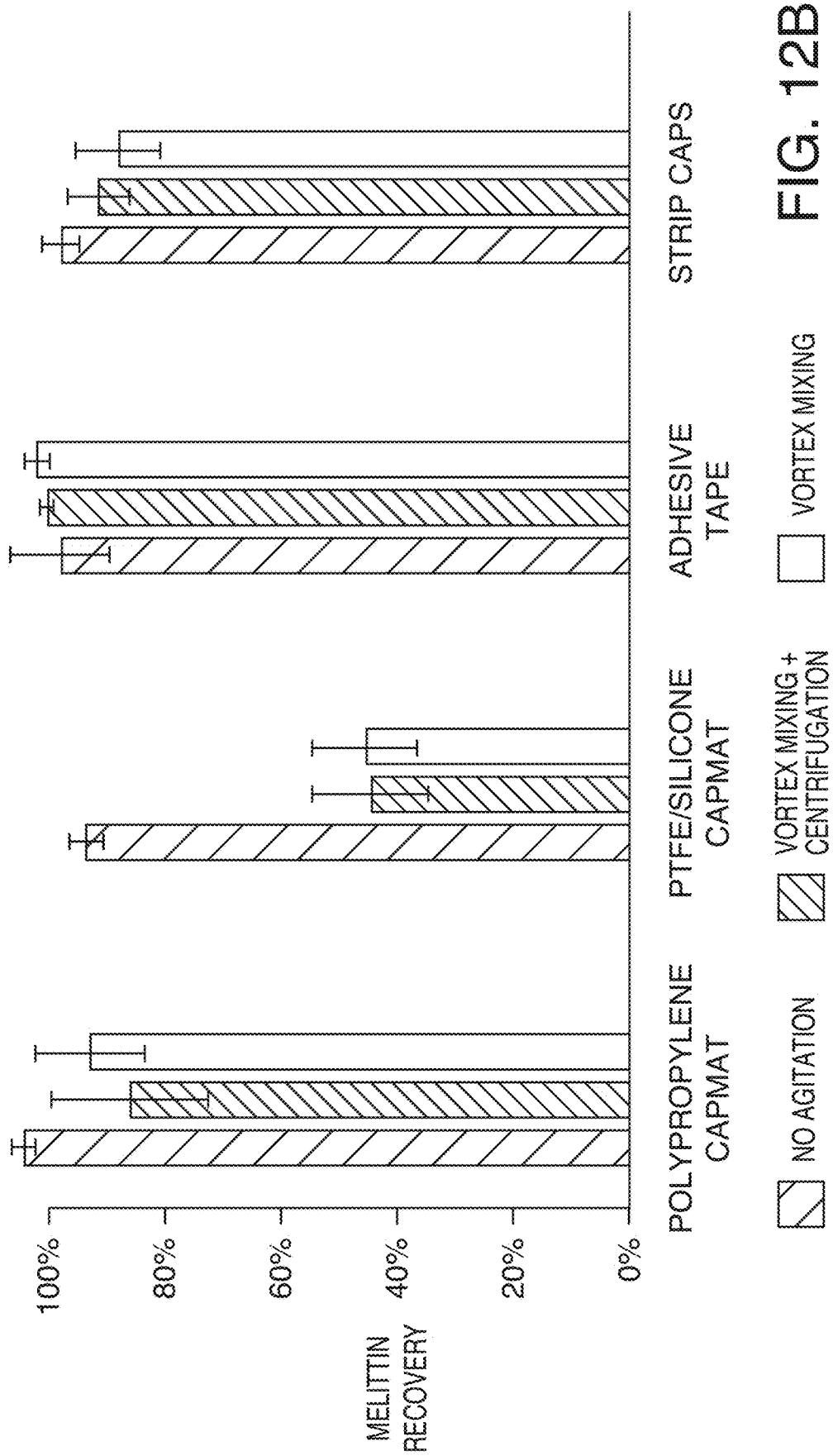
FIG. 12B, is a graph showing average recovery (n=4) of 1 ng/mL melittin in deactivated polypropylene plates capped with various sealing options and physical agitations, according an illustrative embodiment of the technology. The plates were stored at 10° C. for 22 hours before LC-MS analyses. The error bars show the standard deviations. The peptide solutions were prepared in an 80:20 water/acetonitrile mixture and acidified with 0.2% TFA. Tested caps were: 1) a polypropylene cap mat, 2) a PTFE/silicone cap mat, 3) adhesive tape seal, and 4) a strip plug cap. After capping the plates, one plate was left undisturbed; the second plate was agitated by vortex mixing for 5 min and centrifuged at 4000 rpm for 1 min to bring down the solution to the wells, and the third plate was agitated by vortex mixing for 5 min only.

A cap or a sealing mat is an essential, complementary element for a sample container to prevent contamination, evaporation, and accidental splashing. Just as vials have various caps, there are a few sealing options for plates that are also compatible with LC-MS injectors. Generally flat in shape, some sealing caps have embossed structures that match the shape and size of the wells so that the caps are held on top of plates by friction. Other caps are flat films with an adhesive side to attach the film to the plate. Regardless of the shape and sealing mechanism, it is recommended that the caps should not be in direct contact with sample solutions to prevent potential contamination and sample loss. Because sample loss is a particularly important consideration when choosing a low bind product such as a deactivated polypropylene plate of the present technology, several sealing caps were tested to compare peptide losses on the caps. Deactivated polypropylene plates were filled with peptide solutions and four different caps were used to seal the wells. The four caps tested were: 1) a polypropylene cap mat (PN 186002483), 2) a PTFE/silicone cap mat (PN 186006332), 3) adhesive tape seal (PN 186006336), and 4) a strip plug cap. Three plates were identically prepared, and one plate was left undisturbed; the second plate was agitated by vortex mixing and centrifuged to bring down the solution into the wells; and the third plate was agitated by vortex mixing only. After, these three deactivated polypropylene plates were stored for 24 hours (e.g., about 24 hours, such as 22.5 hours, 23 hours, 23.5 hours, 23.8 hours, 23.9 hours, 24.01 hours, 24.2 hours, 24.5 hours, 25.5 hours), the peptide recoveries were measured (FIGS. 12A and 12B showing (1) no agitation, (2) vortex mixing and centrifugation and (3) vortex mixing from left to right on the bar graph for each cap). If the solutions were left undisturbed, the sealing caps did not contribute to peptide losses. When the plates were agitated by vortex mixing, and thus solutions in the well were in contact with the seals, measurable losses were observed. The losses also depended on the hydrophobicity of the peptide: melittin in general was affected more than less hydrophobic teriparatide. Centrifugation after vortex mixing did not prevent the peptide losses once the solutions touched the caps. Some caps showed less peptide losses than others, possibly due to their difference in hydrophobicity and wettability to the tested solutions. In a few test cases, the adhesive tapes showed small leaks around the wells after agitation. It is thus strongly recommended to avoid agitating plates with caps on, and to test the impact if it is unavoidable in the workflow.

Residual Volumes

When selecting a sample container for LC-MS analyses, another factor that should be considered is the residual volume. It is quite common in challenging bioanalyses that the available sample volume is limited. The entire sample volume is not available for LC-MS injection because most LC autosamplers use a sample needle that accesses sample containers from above. This left-over volume is called residual volume, and it is determined by the shape of the container and the needle's vertical position (Z-position). It is therefore important to correctly set the needle position and to select a sample container that is designed to minimize the residual volume. Failure to do so would result in not just waste of precious sample but also inconsistent injections leading to poor assay reproducibility and quantitation errors.

Figure 13:
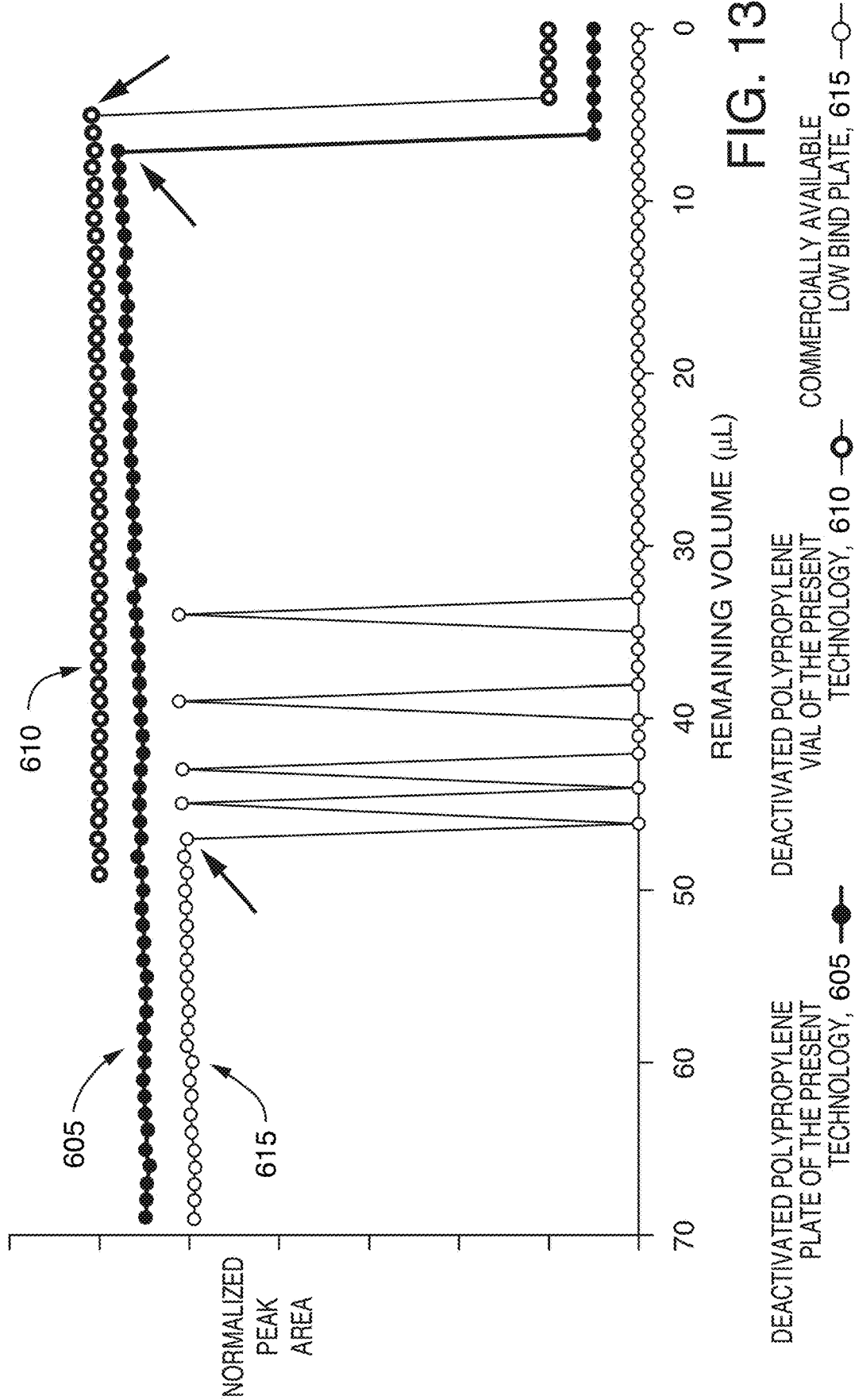
FIG. 13 is a graph showing plots of peak area versus remaining sample volume, using a deactivated polypropylene plate, a deactivated polypropylene vial, and a commercially available low bind plate (commercially available from Eppendorf North America, Hauppauge, N.Y.), according to an illustrative embodiment of the technology. The plates were filled with 70 μL of 0.01 mg/mL caffeine solutions and the vial was filled with 50 μL of the same solution, and a series of 1 μL injections were withdrawn using a flow-through needle in the "partial loop" mode. The needle Z-position was set at 2 mm for the plates and 3 mm for the vial. The peak areas were normalized and plotted with an offset for easy comparison.

The residual volumes of several low bind sample containers were measured. The plates were filled with 70 µL of sample in four corner wells and a center well, and a series of 1 µL injections were withdrawn. Similarly, five vials were filled with 50 µL samples and positioned at four corners and a central position on a 48-vial tray (ANSI-48 Vial 2 mL Holder). The needle Z-position was set to 2 mm for plates and 3 mm for vials. The residual volumes were defined by the remaining volumes when the first unsuccessful injection was made. FIG. 13 shows examples of residual volume measurements for a deactivated polypropylene plate 605, a deactivated polypropylene vial 610, and a commercially available low bind plate 615. Table 1 summarizes the measured residual volumes from all plate wells and vials. The deactivated polypropylene plates and vials showed low average residual volumes (8 and 5 µL, respectively) while the other low bind plate showed a residual volume over 50 µL. Moreover, the standard deviations for residual volumes were much smaller with the deactivated polypropylene plates and vials than with the other low bind plate (about 1 vs 9 µL). This result, in addition to the greater recovery for peptides in small sample volumes (see, FIG. 11), demonstrates that deactivated polypropylene plates and vials are ideal choices when analyzing samples with a limited volume.

TABLE 1

Summary of Measured Residual Volumes from Each Well and Vial

| | Polypropylene plate of the present technology | Polypropylene vial of the present technology | Commercially available low bind plate |
|---|---|---|---|
| Top-left | 10 | 5 | 54 |
| Top-right | 7 | 4 | 47 |
| Bottom-left | 7 | 5 | 45 |
| Bottom-right | 9 | 5 | 52 |
| Center | 9 | 6 | 68 |
| Average | 8.3 | 5.0 | 53.2 |
| Standard deviation | 1.3 | 0.7 | 9.0 |

Referring to Table 1, position #1 was at the top left corner (plate position A,1 or vial position #1), #2 at the top right (A,12 or #43), #3 at the bottom left (H,1 or #6), #4 at the bottom right (H,12 or #48), and #5 in the center (D,6 or #21).

Quantitative LC-MS analyses for proteins and peptides is challenging, requiring greater sensitivity and reproducibility from smaller amounts of samples. Analyte loss due to nonspecific binding in sample containers is a significant problem in quantitation that is often not recognized early enough. Failure to mitigate this problem can lead to hours of wasted time during method development, or even worse, to suboptimal methods that are limited by poor analytical sensitivity and reproducibility. Understanding the mechanisms and the kinetics of the losses provided useful guidelines to mitigate this problem. Some experimental factors, such as sample matrix, storage temperature and sealing options may be readily varied within the workflow to maximize the recoveries. Other factors, such as storage time, sample volume and peptide concentration may not be modified because the available options are dependent on other steps in the total workflow. While using containers that are designed to mitigate NSB cannot prevent all adsorption problems, it certainly allows more options than would be available if using other containers.

Applications

The deactivated polypropylene plates and vials can be used for a variety of peptides, for example, endogenous peptides such as vasopressin, somatostatin, angiotensin, renin substrate, glucagon, insulin, melittin; synthetic peptides such as pramlintide, desmopressin, octreotide, teriparatide, enfuvirtide bivalirudin; and tryptic peptides. The deactivated polypropylene plates and vials can be used for a variety of proteins, for example, endogenous and synthetic proteins; therapeutic proteins such as monoclonal antibodies and their subunits and fragments, antibody-drug conjugates, fusion proteins, bispecific antibodies, oligonucleotides, and lipids.

The deactivated polypropylene plates and vials can be used in a wide range of other applications, for example proteomics, metabolomics, peptidomics, lipidomics, biopharmaceutical characterization, peptide mapping, intact analysis, variant analysis, and quantitative assay. In addition, applications can include applications within material science, pharmaceuticals, biopharmaceuticals, food & environmental, clinical and biomedical research. More specifically, applications within academic studies, drug discovery, development, bioanalysis, characterization, in-process monitoring, in-process testing, quality assurance, quality control, clone-selection, clone-development, diagnostic testing, diagnostic development, laboratory-developed testing, biological studies, up/down regulations studies, excipient analysis, protein analysis, polymer analysis, assay development, assay testing, plate reader analysis, ELIZA studies, sandwich assays, culture studies, and culture growth are contemplated. Applications can also include impurity analysis and degradation analysis.

Example 1: Development of a SPE LC-MS/NIS Method for the Bioanlytical Quantification of Pramlintide from Serum Pramlintide acetate (SYMLIN™ commercially available from AstraZeneca) is a 37 amino acid (MW 3949.4 Da) synthetic analogue of the human hormone amylin. Developed as an adjunctive therapy for patients with type 1 and 2 diabetes, this peptide can improve treatment outcomes for those who have failed to achieve glycemic control despite optimal insulin therapy. With nearing patent expiry dates for pramlintide, and recent research indicating a role for amylin in Alzheimer's Disease models, interest in amylin and amylin agonists is rising. Characterized by fast absorption (<30 minutes), elimination (~1 hour), and low circulating levels (pg/mL), amylin agonists such as pramlintide can be challenging to quantify. LC-MS/MS assays have become increasingly popular for peptide quantification due to the high sensitivity and specificity afforded by selective MRM fragments. However, method development and accurate quantification for hydrophobic peptides like pramlintide can still be challenging because peptides notoriously suffer from non-specific binding (adsorption). This can lead to poor recovery, loss of analyte, and poor limits of detection. This example uses a selective sample preparation strategy and LC-MS compatible sample storage plates with deactivated polypropylene surfaces to mitigate pramlintide loss due to non-specific binding. In addition to this, optimized HPLC separation and column chemistry, along with a highly sensitive tandem quadrupole mass spectrometry method can produce significantly lower limits of quantification. For this assay, an LLOQ of 25 pg/mL of pramlintide was achieved, extracted from 100 µL of rat and human serum.

Sample Preparation

Calibration curve standards and quality control (QC) samples of pramlintide (ProSpec Bio, Rehovot, Israel, P/N: HOR-300) were prepared in commercially available human and rat serum at various concentration levels (25-50,000 pg/mL). All calibration curve standards, QC levels, and blank (non-spiked) samples were prepared in triplicate.

Solid Phase Extraction (SPE)

100 µL of serum was diluted with 100 µL of water and vortexed. All wells of a 96-well OASIS® WCX µElution Plate (P/N: 186002482 commercially available from Waters Technologies Corporation, Milford, Mass.) were conditioned with 200 µL of methanol and then equilibrated with 200 µL of water. The diluted serum samples (200 µL) were loaded onto the SPE plate, subsequently washed with 200 µL of water, and followed by 200 µL of 20% acetonitrile in water. Pramlintide was eluted from the sorbent using a 1×25 µL aliquot of the elution solvent containing 1% trifluoroacetic acid in 75:25 (v/v) acetonitrile:water. Eluates were collected in a deactivated polypropylene LC-MS compatible sample plate in accordance with the present technology, and then diluted with 25 µL of water for a final sample volume of 50 µL. 10 µL of each sample were injected onto an ACQUITY® UPLC® I-Class PLUS liquid chromatography system equipped with a 2.1×50 mm Peptide CSH C18 column (P/N: 186006936 commercially available from Waters Technologies Corporation, Milford, Mass.) and a Xevo® TQ-XS mass spectrometer (commercially available from Waters Technologies Corporation, Milford, Mass.).

LC/MS Method Conditions

| LC System: | ACQUITY ® UPLC ® I-Class PLUS (Fixed Loop) system |
|---|---|
| Detection: | Xevo ® TQ-XS Mass Spectrometer, ESI+ |
| Column: | ACQUITY ® UPLC ® Peptide CSH $C_{18}$, 130 Å, 1.7 µm, 2.1 × 50 mm Column |
| Column Temp: | 60° C. |
| Sample Temp: | 15° C. |
| Injection Volume: | 10 µL |
| Mobile Phases: | A: 0.1% Formic Acid in Water<br>B: 0.1% Formic Acid in Acetonitrile |

| MS system: | Xevo TQ-XS |
|---|---|
| Ionization mode: | ESI+ |
| Capillary (kV) | 1.0 |
| Cone (V) | 15 |
| Source Offset (V) | 30 |
| Source Temperature (° C.) | 150 |
| Desolvation Temperature (° C.) | 600 |
| Cone Gas Flow (L/Hr) | 150 |
| Desolvation Gas Flow (L/Hr) | 1000 |
| Collision Gas Flow (mL/Min) | 0.15 |
| Nebuliser Gas Flow (Bar) | 7 |
| System Calibration: | Low Resolution |
| Data Management | MassLynx (v4.2) |
| Quantification Software | TargetLynx XS |

LC Gradient

| Time (min) | Flow Rate (mL/min) | % A | % B | Curve |
|---|---|---|---|---|
| Initial | 0.400 | 80.0 | 20.0 | 6 |
| 0.50 | 0.400 | 80.0 | 20.0 | 6 |
| 1.00 | 0.400 | 78.0 | 22.0 | 6 |
| 4.00 | 0.400 | 73.0 | 27.0 | 6 |
| 4.75 | 0.400 | 5.0 | 95.0 | 6 |
| 5.50 | 0.400 | 5.0 | 95.0 | 6 |
| 6.00 | 0.400 | 80.0 | 20.0 | 6 |
| 7.00 | 0.400 | 80.0 | 20.0 | 6 |

MS Conditions

| Precursor (m/z) | Product (m/z) | Cone Voltage (V) | Collision Energy (eV) | Product Ion Identification | |
|---|---|---|---|---|---|
| 988.36 | 968.11 | 15 | 20 | [3H+]3/b27 | Primary |
| 988.36 | 930.78 | 15 | 26 | [4H+]4/y35 | Confirmatory |

Sample Handling: Deactivated Polypropylene Plates of the Present Technology

Larger and more hydrophobic molecules, including peptides, often suffer from non-specific binding (NSB) or adsorption to any labware that samples come into contact with (for example, plates, vials, pipette tips). As discussed above, a commonly used strategy to mitigate the effects of non-specific binding of our molecules of interest is to add carrier protein(s) to the sample. This can be done prior to sample clean up and/or immediately prior to LC-MS/MS analysis of the analyte. Although generally highly effective, adding carrier proteins to a sample also adds more complexity to the sample.

Figure 14:
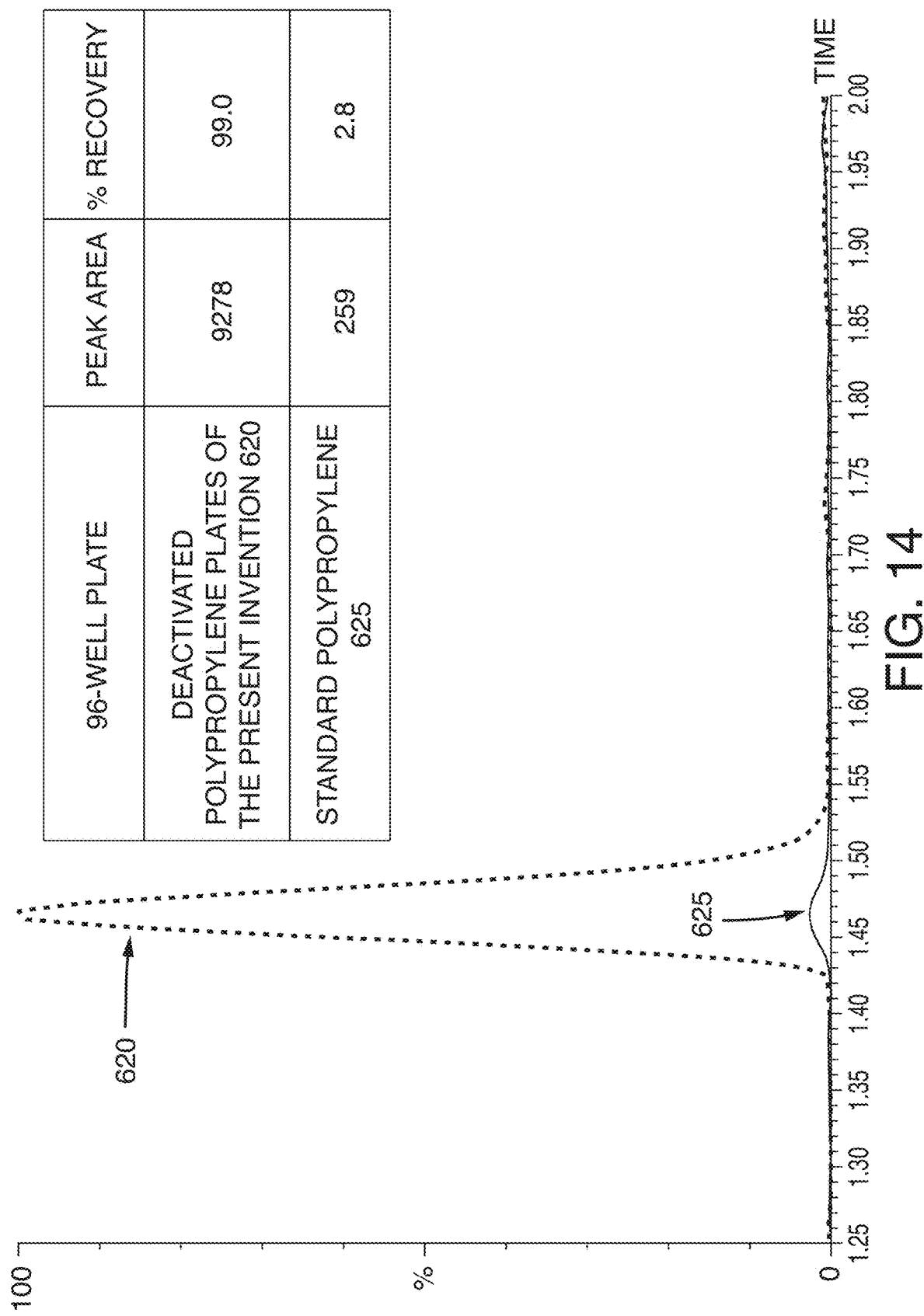
FIG. 14 is a chromatogram showing the recovery of pramlintide using a standard polypropylene plate and a deactivated polypropylene plate of the present technology, according to an illustrative embodiment of the technology.
Figure 15A:
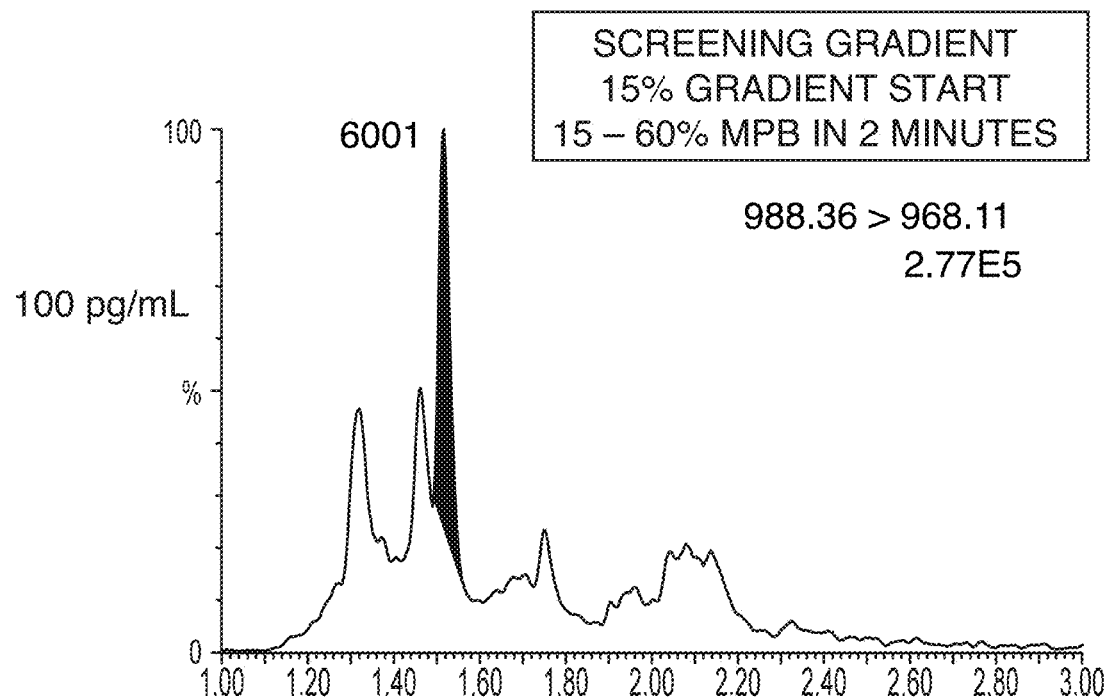
FIGS. 15A and 15C are chromatograms of 100 pg/mL pramlintide extracted from rat serum and separated using a screening chromatography gradient (FIG. 15A) and an optimized gradient (FIG. 15C), according to an illustrative embodiment of the technology.
Figure 15B:
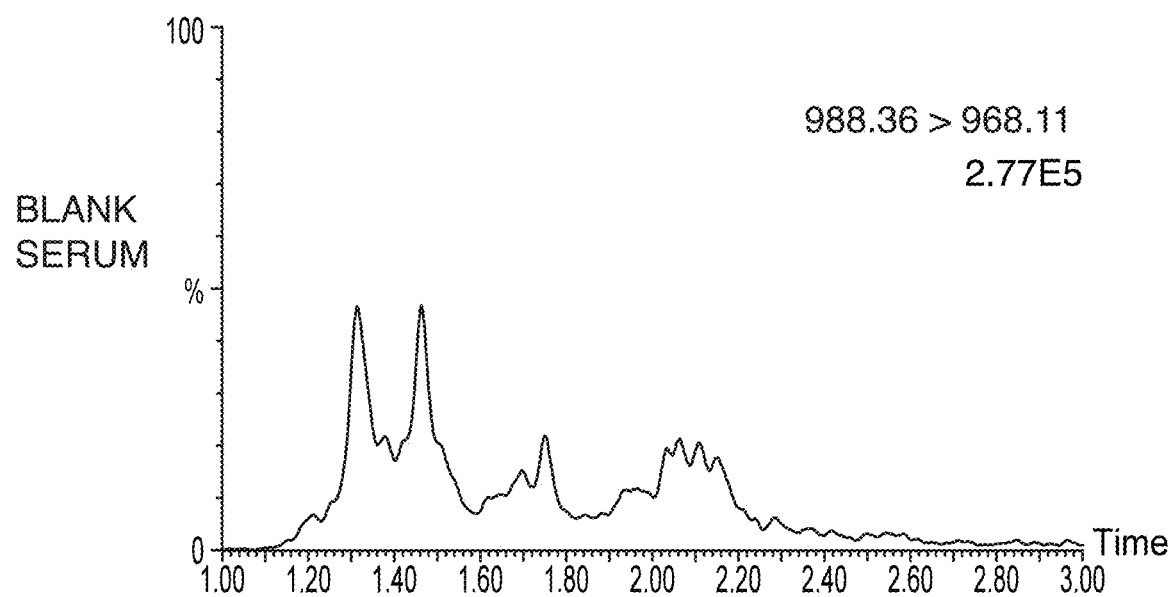
FIGS. 15B and 15D are chromatograms of a blank serum and separated using a screening chromatography gradient (FIG. 15B) and an optimized gradient (FIG. 15D), according to an illustrative embodiment of the technology. The optimized gradient significantly improved matrix suppression from ~20% to less than 10%, and decreased the chromatographic baseline to acceptable levels.
Figure 15C:
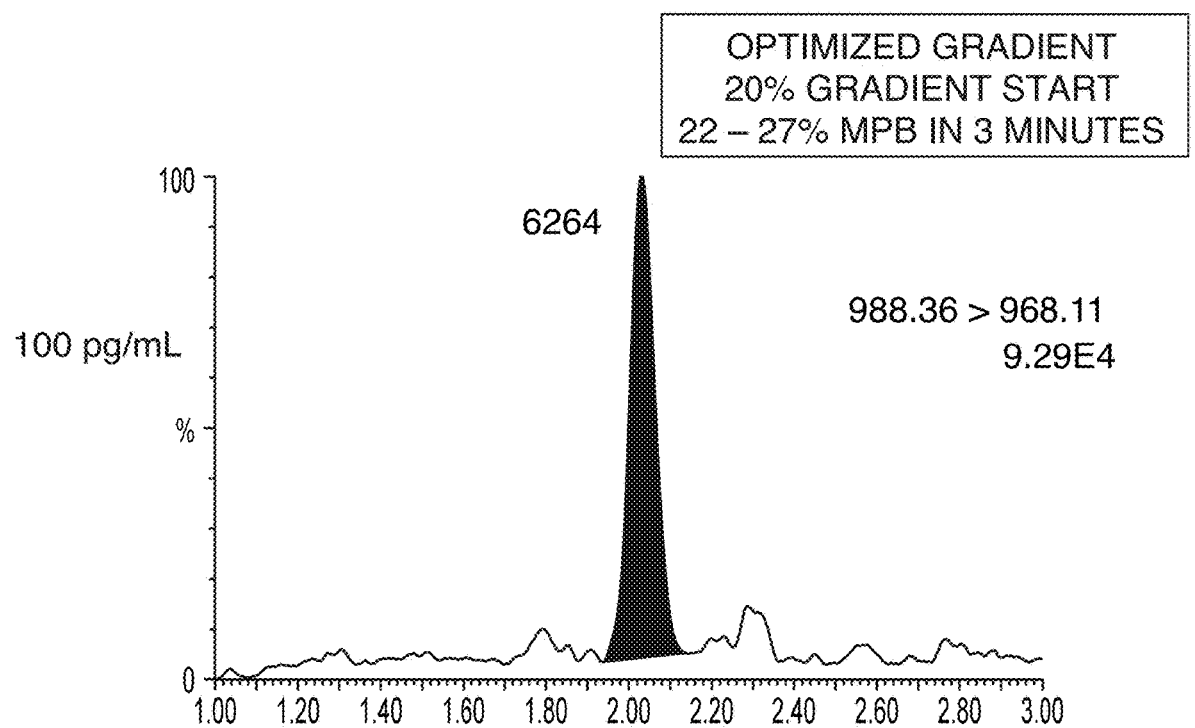
Figure 15D:
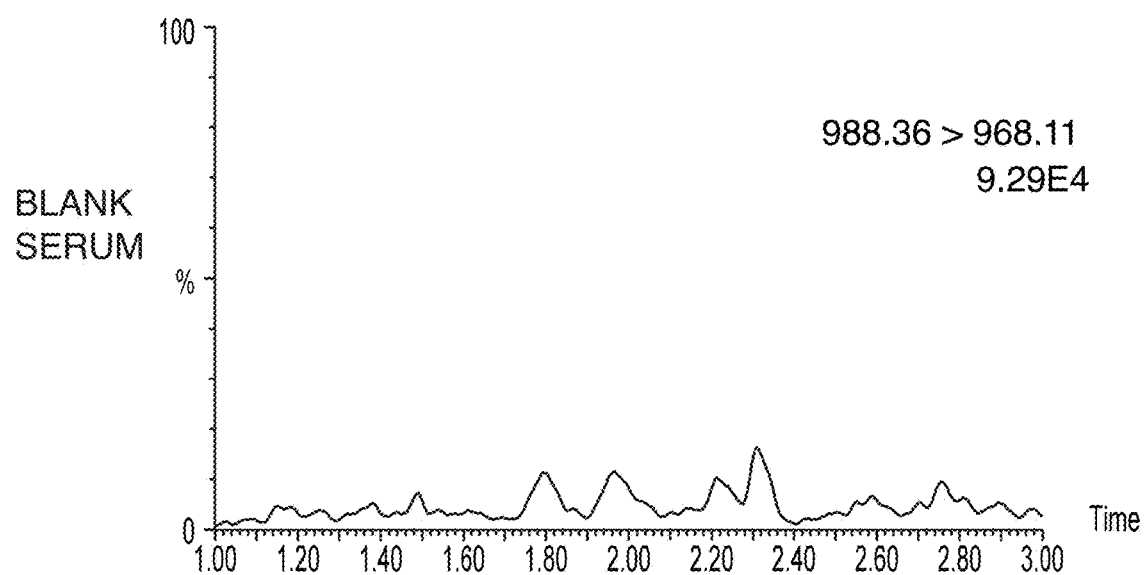
Figure 16A:
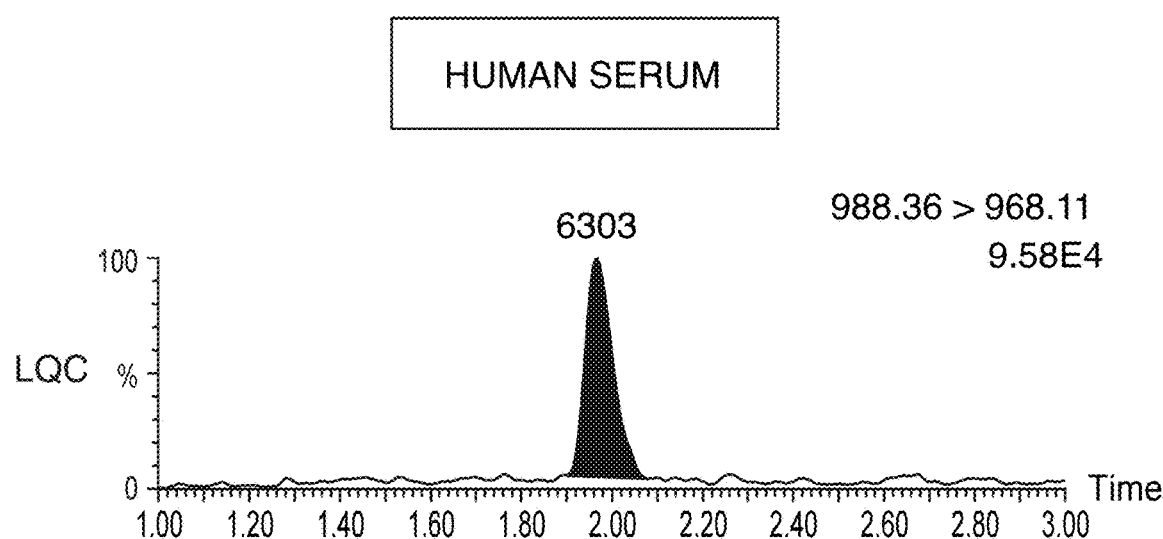
FIGS. 16A-16C are chromatograms showing representative LQC (FIG. 16A), LLOQ (FIG. 16B), and blank (FIG. 16C) chromatograms for pramlintide extracted using OASIS® WCX μElution SPE (commercially available from Waters Technologies Corporation, Milford, Mass.) from 100 µL of human serum, according to an illustrative embodiment of the technology.
Figure 16B:
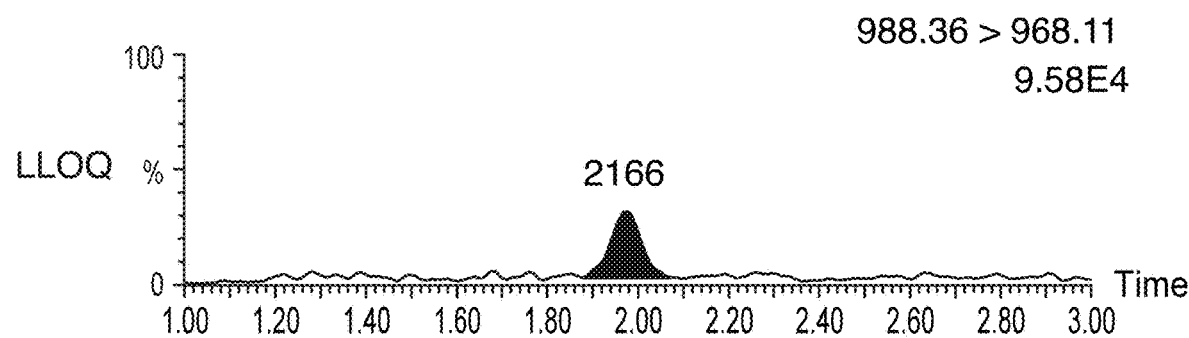
Figure 16C:
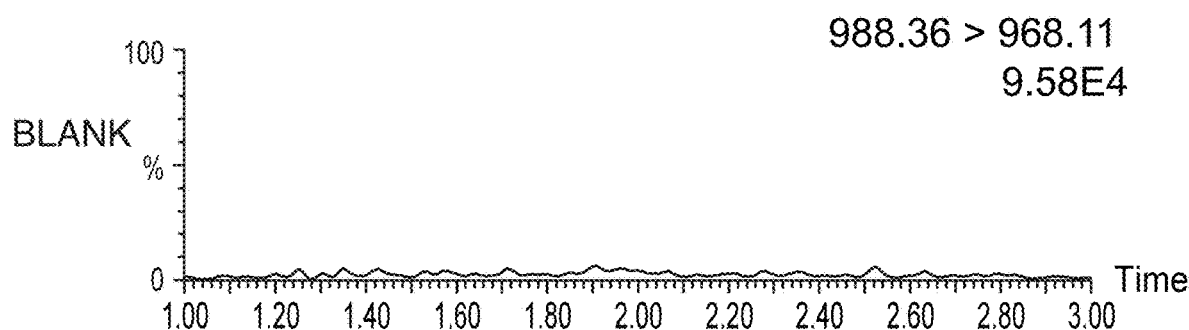
Figure 16D:
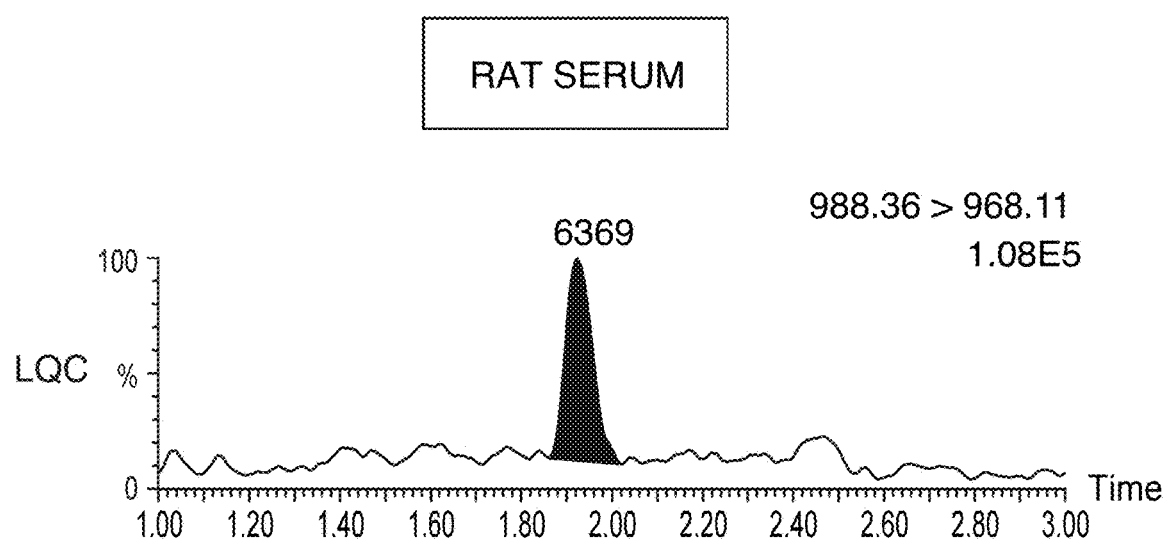
FIGS. 16D-16F are chromatograms showing representative representative LQC (FIG. 16D), LLOQ (FIG. 16E), and blank (FIG. 16F) chromatograms for pramlintide extracted using OASIS® WCX µElution SPE (commercially available from Waters Technologies Corporation, Milford, Mass.) from 100 µL of rat serum, according to an illustrative embodiment of the technology.
Figure 16E:
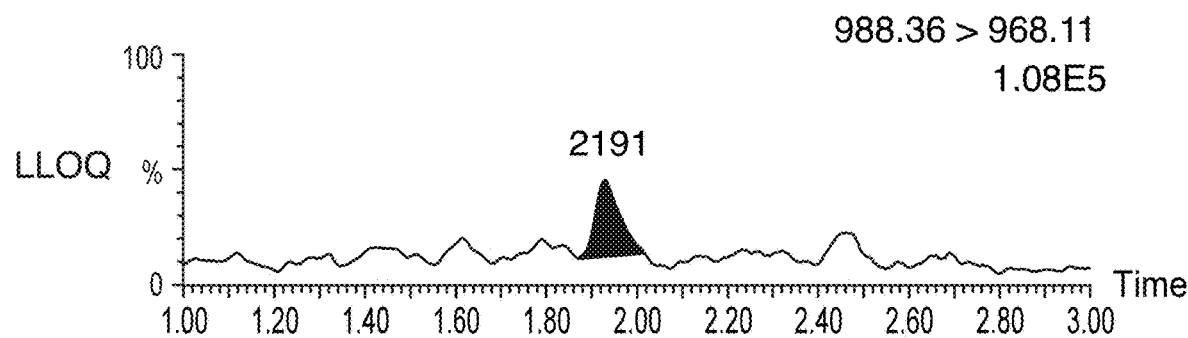
Figure 16F:
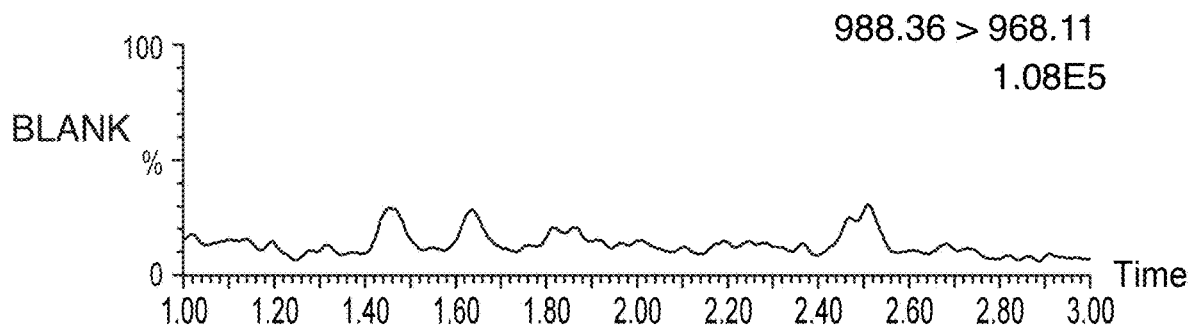

Pramlintide is a large peptide (MW 3949.4 Da) which is hydrophobic (HPLC Index: 88.7) and can therefore be expected to suffer from some degree of non-specific binding. During method development, pramlintide was stored in either a deactivated polypropylene plate or a standard polypropylene plate prior to LC-MS/MS analysis in order to assess the plates' effectiveness in mitigating NSB. Test samples were prepared and stored in neat solution, while additional samples prepared in a solution containing carrier proteins were used as a benchmark for 100% recovery. Results from this assessment showed that pramlintide suffered from a high degree of NSB to a standard polypropylene plate, while the deactivated polypropylene plate was able to significantly mitigate the effects of NSB as seen in FIG. 14. Recovery of 10 ng/mL pramlintide from the deactivated polypropylene plate 620 was almost 100%, leading to a peak area ~36 times higher than samples stored in a standard polypropylene plate 625 where analyte recovery was only ~3%. Although this strategy combats pre-analytical NSB of our peptide of interest, it is important to keep in mind that peptides can adsorb to any surface they come in contact with prior to entering the mass spectrometer (including any plate transfer steps or system loss). For all analytes, it is important to determine if pre-analytical mitigation of non-specific binding is enough to reach the desired limits of detection of your assay. In some cases, it may still be necessary to use both carrier protein addition and high performance surface sample storage containers to ensure that an analyte is not lost due to adsorption. Pramlintide benefits from the use of deactivated polypropylene plates and vials post SPE extraction to reach the desired limits of detection of this assay.

Solid phase extraction (SPE) is a simple, robust, and fast sample preparation method which can be used to extract analytes from complex matrices. Waters OASIS® Peptide Separation Technology (PST) µElution SPE screening strategy (Table 2), specifically designed for peptides, provides a simple method to quickly screen multiple SPE sorbents (Oasis® MAX and WCX) to assess recovery and matrix effects of their peptide of interest. Using this strategy, pramlintide was screened and resulted in starting recoveries of ~46 and 58%, respectively. The calculated isoelectric point (pI) of pramlintide is 10.2 indicating that this peptide will be positively charged under most SPE conditions. Due to this, and the higher recovery achieved in the initial screening experiment, the weak cation exchange sorbent (WCX) was best suited for the extraction of pramlintide.

TABLE 2

SPE Protocols and Results

| Acids<br>pkA 2-8<br>OASIS Max | Strong Bases<br>pKa >10<br>OASIS WCX |
|---|---|
| 46% Recovery | 58% Recovery |

OASIS PST Protocol

Load: Dilute serum with 4% $H_3PO_4$
Wash 1: 5% $NH_4OH$
Wash 2: 20% ACN
Elute 1% TFA in 75:25 ACN:$H_2O$ Through additional optimization experiments, it was determined that pramlintide was not adequately retained on the WCX sorbent during sample loading and wash 1 with 5% $NH_4OH$ (pH ~12). Pramlintide is a basic peptide, as indicated by its pI, it is largely negatively charged at this pH, leading to poor retention on the negatively charged SPE sorbent. Changing the pretreatment solution and wash 1 solvent to water (pH<7) ensured that the sorbent remained negatively charged, and pramlintide remained positively charged during both loading and wash 1. Wash 2 and the elution solution used in the PST protocol remain the same in the optimized protocol, as it was determined during method optimization that trifluoroacetic acid was effective at fully eluting pramlintide from the SPE sorbent. Weaker acids such as formic acid and acetic acid were assessed and resulted in very low recoveries of the analyte (<10%). With the combination of this optimized protocol and chromatography gradient (discussed below), recovery of pramlintide was improved to ~75% (Table 3).

TABLE 3

SPE Protocol and Results

Pramlintide
pI: 10.2
OASIS WCX
75% recovery
Optimized Protocol

Load: Dilute serum with water
Wash 1: Water
Wash 2: 20% ACN
Elute: 1% TFA in 75:25 ACN:$H_2O$ During method development of pramlintide, several reversed phase columns were assessed for overall chromatographic performance (not shown). It was determined that the Peptide CSH C18 column, with its positively charged surface, provided the best selectivity and sensitivity, with a 5-fold improvement in signal to noise compared to the Peptide BEH C18 column.

Despite the improved selectivity and sensitivity afforded by the Peptide CSH C18 column, matrix interferences from extracted serum samples were still high, leading to signal suppression. During method development, a screening gradient from 15-60% mobile phase B (MPB) over 2 minutes was used. Initial results determined there was significant signal suppression (~20%) as compared to a non-extracted pramlintide sample. Modifying the gradient and increasing the starting percentage of organic solvent MPB from 15 to 20% significantly decreased the matrix background entering the mass spectrometer. In order to properly separate pramlintide from remaining matrix interferences at very low concentrations, the gradient was shallowed to 22-27% MPB over 3 minutes. The combination of selective column chemistry and a highly optimized gradient resulted in reduction of observed matrix suppression (<10%) and improved pramlintide peak area, greatly improving both selectivity and sensitivity (FIGS. 15A-15D).

Mass Spectrometry

LC-MS/MS quantification of pramlintide was performed using a Xevo® TQ-XS mass spectrometer and low resolution calibration (1.0 Da at FWHM) to achieve better assay sensitivity. When working with a lower resolution system calibration, it is critically important to use selective MRM fragments with high m/z values for quantification in order to avoid high background and matrix interferences. During method development, three predominant precursors were observed at 1317.48 (3+), 988.36 (4+), and 790.89 (5+) m/z, with the 4+ precursor resulting in the most intense fragments. Via manual tuning, an intense fragment of the 4+ precursor was identified at 968.11 m/z, corresponding to the b-ion cleavage between Leu-27 and Pro-28. This highly selective and intense fragment of pramlintide was used as the primary quantification transition, while the y-ion transition at 930.78 m/z was used as a qualifier. Optimized MS conditions and MRM transitions used for quantification of pramlintide are listed above.

Linearity, Precision, and Accuracy

Linear, precise, and accurate quantification of pramlintide was achieved using only 100 µL of human or rat serum. Limits of detection (LOD) of 10 pg/mL and lower limits of quantification (LLOQs) of 25 pg/mL were achieved for both human and rat serum. Calibration curves were linear ($r^2$>0.99) from 25-50,000 pg/mL using a $1/X^2$ linear fit (Table 4). All calibration curves and QC levels were accurate within ±15% and CVs were <5%. QC performance is highlighted in Table 5 where all statistics met recommended bioanalytical method validation guidelines, and chromatographic performance is illustrated in FIGS. 16A-16F.

TABLE 4

Standard Curves
Calibration Curve Statistics

| Species | Curve (pg/mL) | Weighting | Linear Fit ($r^2$) | % Accuracy Range |
|---|---|---|---|---|
| Human | 25-50,000 | $1/X^2$ | 0.995 | 91.3-111.0 |
| Rat | 25-50,000 | | 0.996 | 92.3-105.9 |

TABLE 5

QC Statistics

| QC Level | QC Concentration (pg/mL) | Mean (N = 3) calculated QC Concentration (pg/mL) | Mean (N = 3) % Accuracy | Mean (N = 3) % CV |
|---|---|---|---|---|
| A: Human Serum QC Statistics | | | | |
| LLOQ | 25 | 24.0 | 96.1 | 3.5 |
| LQC | 75 | 77.4 | 103.3 | 5.0 |
| MQC | 2500 | 2619.1 | 104.8 | 1.1 |
| HQC | 40000 | 39309.7 | 98.3 | 2.8 |
| B: Rat Serum QC Statistics | | | | |
| LLOQ | 25 | 23.5 | 93.9 | 3.7 |
| LQC | 75 | 72.2 | 96.2 | 3.1 |
| MQC | 2500 | 2512.6 | 100.5 | 5.2 |
| HQC | 40000 | 36628.5 | 91.6 | 1.7 |

This example describes a simple sample preparation strategy using OASIS® WCX µElution SPE and the deactivated polypropylene plates of the present technology. Combining this approach with UPLC® liquid chromatographic separation and a tandem quadrupole MS resulted in high sensitivity quantification of pramlintide from human and rat serum. Sample preparation with simple SPE allowed for fast extraction (<2 hours) of pramlintide from complex matrices. The deactivated polypropylene plates effectively mitigated non-specific binding and provided a 36-fold increase in pramlintide peak area in neat solution. Use of a sub-2-µm ACQUITY® UPLC® Peptide CSH $C_{18}$ Column and optimized chromatography gradients provided improved analyte selectivity and a significant decrease in matrix suppression of the assay. Using only 100 µL of human (or rat) serum, a LLOQ of 25 pg/mL was achieved with excellent precision (CVs<5%) and accuracy.

Example 2: Non-Specific Binding of Biotherapeutics Using LC-MS and Deactivated Polypropylene Plates of the Present Technology Larger, hydrophobic biomolecules, such as monoclonal antibodies (mAbs), often suffer from non-specific binding (NSB) or adsorption to any labware that samples come into contact with. This makes LC-MS method development challenging, and negatively impacts analytical performance. Ensuring labware (plates, vials, pipette tips, etc. . . . ) is designed specifically to minimize NSB can greatly improve assay performance.

Biotherapeutics are becoming more complex as they are engineered to improve efficacy at safer dosage levels. To support development of these drugs, more sensitive and selective assays are required to meet needed limits of detection. Larger, hydrophobic biomolecules, such as monoclonal antibodies (mAbs), often suffer from non-specific binding (NSB) or adsorption to any labware that samples come into contact with (plates, vials, pipette tips, etc. . . . ). This phenomena is dependent on the physicochemical properties of the molecules and typically increases in severity at low concentrations. This can lead to poor recovery, loss of analyte, and poor assay reproducibility, ultimately leading to insufficient limits of detection. It is therefore important to mitigate the effects of NSB wherever possible. A commonly used approach to combat NSB is to add carrier protein into samples. Carrier proteins will coat the surfaces that samples come into contact with and decrease the amount of the molecule of interest that is adsorbed to these surfaces. Although generally effective, this strategy adds unwanted complexity back into the samples. To minimize the need for this, samples can be prepared and stored prior to LC-MS/MS analysis in sample storage containers with the deactivated polypropylene plates and vials to mitigate the effects of NSB and increase analyte recovery and reproducibility by minimizing analyte/surface interactions that can lead to sample losses.

In this example, deactivated polypropylene plates were used to mitigate non-specific binding of several mAbs prior to LC-MS/MS analysis. Quantification of adalimumab, cetuximab, and the NISTmAb (RM 8671, P/N: 186009125), was performed at the subunit light chain level using a Xevo® TQ-XS mass spectrometer and a common MS/MS fragment (1329.85 m/z) from the conserved region of the mAb light chains. Chromatographic separation was achieved using an ACQUITY® UPLC® I-Class Plus System with a BioResolve® RP mAb Polyphenyl, 450 Å, 2.7 µm, 2.1×50 mm Column (P/N: 186008944 commercially available from Waters Technologies Corporation, Milford, Mass.). A shallow gradient of 25-30% B over 2.5 minutes (flow rate 0.4 mL/min) was used to separate biotherapeutics with mobile phases of water and acetonitrile containing 0.1% formic acid.

Figure 17:
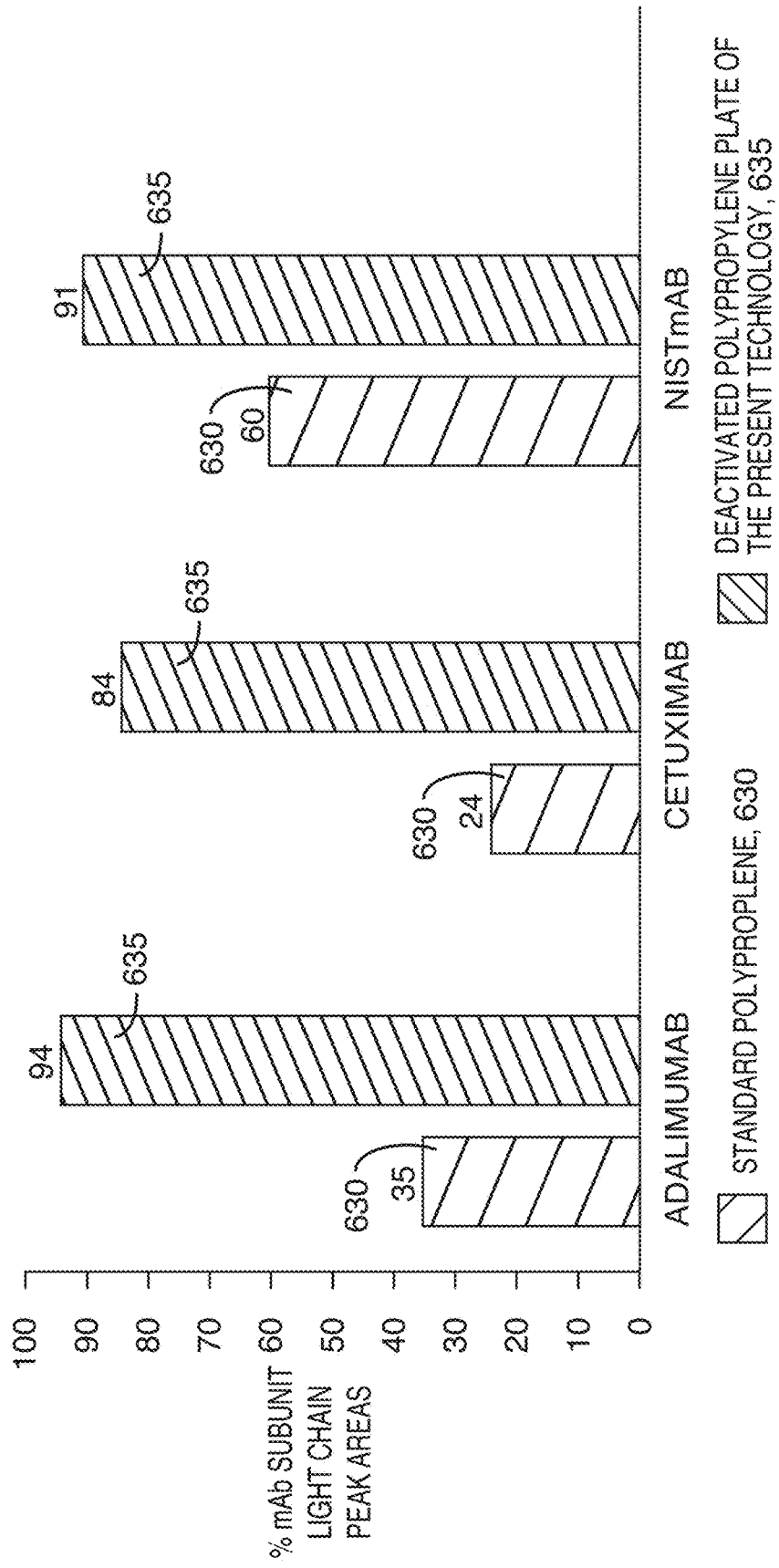
FIG. 17 is a graph showing recovery of intact biotherapeutics from standard polypropylene sample plates and deactivated polypropylene plates of the present technology, according to an illustrative embodiment of the technology. Adalimumab, cetuximab, and NISTmAb (100 ng/mL) were prepared in neat solution and incubated in test plates. A solution containing carrier protein was used as a benchmark for 100% recovery.

During method development, the three mAbs were stored in either a deactivated polypropylene plates or a standard polypropylene plate in order to assess the plates' effectiveness in mitigating NSB at the intact mAb level. Test samples (100 ng/mL) were prepared and stored in neat solution, while additional samples prepared in a solution containing carrier proteins were used as a benchmark for 100% recovery. Shown in FIG. 17, samples stored in deactivated polypropylene plates 635 for 24 hours experienced very little NSB with 84-94% recovery, while samples stored in a standard polypropylene plate 630 suffered from variable levels of NSB ranging from only 23-60% recovery.

With these results in mind, and as further demonstration of deactivated polypropylene plates performance, each of the three mAbs were extracted from rat plasma and the resulting samples were stored in deactivated polypropylene plates prior to LC-MS/MS analysis. Biotherapeutics were immunopurified from rat plasma (10 µL) using biotinylated anti-human Fc Ab (15 µL) conjugated to streptavidin coated magnetic beads (25 µL). Affinity purified samples (50 µL) were reduced and alkylated using the ProteinWorks Auto-eXpress Digest Kits' (P/N: 186008889) reagents. Samples were reduced to light and heavy chains with dithiothreitol, then alkylated with iodoacetamide for stability. A 10 µL aliquot of the resulting 70 µL of sample was injected directly from deactivated polypropylene plates for each LC-MS/MS analysis. With these optimized sample preparation methods, storage conditions, and LC-MS/MS methods, LLOQs of 25-50 ng/mL were achieved for all three study mAbs. Calibration curves were linear ($r^2$>0.99) from 25-100,000 ng/mL and statistics indicate excellent accuracy (±15%) and precision with CVs<10% (Table 1). Although the level of NSB mitigation experienced using deactivated polypropylene plates sample plates is mAb specific, there is a clear benefit to using deactivated polypropylene plates for this type of molecule, particularly at low protein concentrations. Table 6 shows the biotherapeutic fragment identification. Table 7 shows calibration curve statistics.

TABLE 6

Biotherapeutic Fragment Identification

| Biotherapeutic | Precursor (m/z) | Fragment (m/z) | Fragment Identity |
|---|---|---|---|
| Adalimumab | 1236.02 | 1329.85 | P119-y96 |
| Cetuximab | 1236.81 | | |
| NIST mAb | 1288.84 | | |

UV-inactive nature, direct analysis of PS-20 has resulted in methods that incorporate alternative detection techniques such as evaporative light scattering detection (ELSD). Yet, given the ubiquitous nature of UV/MS-based instruments in pharmaceutical labs, methods that can utilize existing equipment would be beneficial. Conveniently, the hydrophobic ester tail of PS-20 can be cleaved through a hydrolysis process (shown below) to produce the UV-active fatty acid, lauric acid, which is UV/MS active and offers a relatively simple MS spectrum for easy interpretation or integration to determine the amount of trace level impurities that may be present in drug substance or product.

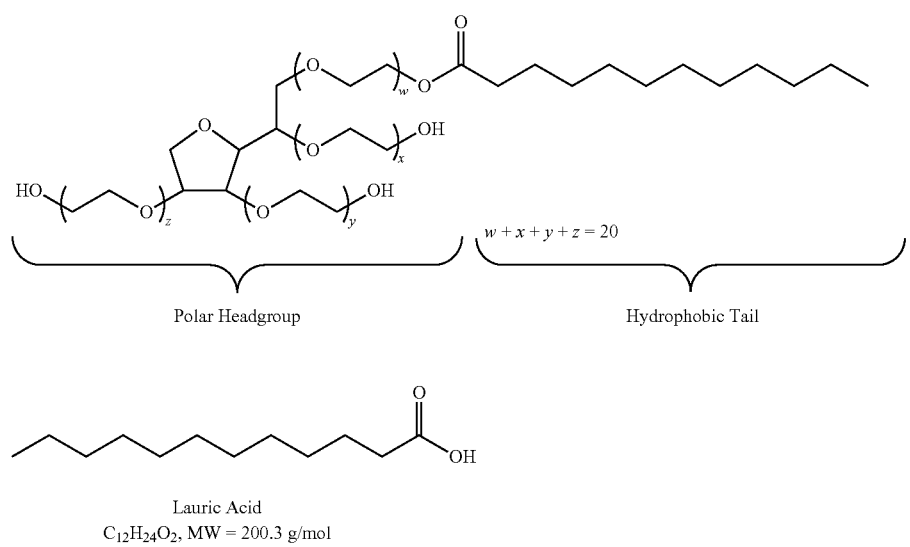

Lauric Acid
$C_{12}H_{24}O_2$, MW = 200.3 g/mol

TABLE 7

Calibration Curve Statistics

| Biotherapeutic | Curve (ng/mL) | Weighting | Linear Fit ($r^2$) | % Accuracy Range |
|---|---|---|---|---|
| Adalimumab | 25-100,000 | $1/X^2$ | 0.997 | 94.5-104.3 |
| Cetuximab | 25-100,000 | | 0.996 | 95.7-105.5 |
| NIST mAb | 50-100,000 | | 0.996 | 93.9-105.9 |

Example 3: Non-Specific Binding of Fatty Acids Using Deactivated Polypropylene Plates of the Present Technology Surfactants such as polyoxyethylene sorbitan monolaurate (PS-20) are commonly used in formulated biopharmaceuticals to reduce protein denaturing, aggregation, and surface adsorption to vials and syringes. While PS-20 plays a critical role in stabilizing drug products, degradation of surfactants in formulated drugs can decrease overall product efficacy and safety. To this end, characterization, identification, and quantitation of excipients such as PS-20 must be performed to demonstrate the drug product is safe and efficacious in its formulated state. Due to its non-volatile and UV-inactive nature, direct analysis of PS-20 has resulted in Fatty acids have mixed physicochemical properties as they contain a hydrophobic alkyl chain and carboxyl group which can be protonated or deprotonated depending on pH of the sample matrix. This can be problematic in LLEs as impurities at trace levels can be lost to sample container walls leading to inaccurate assessment of impurities present in drug substance or products. Given this, using containers throughout the sample preparation process are critical in ensuring results are consistent, reproducible, and accurate.

To compare performance of the deactivated polypropylene vials to conventional vials in the recovery of free fatty acids, a serial dilution of lauric acid was performed and evaluated.

A stock solution of lauric acid was prepared by mass at a concentration of 16000 ppm wt/wt in a 20 mL conical tube.

A serial dilution of the stock solution was carried out in LoBind Eppendorf tubes by aliquoting a predetermined volume of stock solution and performing 2 fold dilutions in order to achieve concentrations down to 0.06 ppm.

300 uL of each dilution were then aliquoted into both LCGC and the deactivated polypropylene vials and vortexed. Sample dilution series from 7.81 ppm to 0.06 ppm were chosen to evaluate trace level detection between the deactivated polypropylene vials and conventional LC/GC certified vials.

Diluent used in the study was comprised of a preoptimized MS-grade solvent for fatty acid analysis containing 75:25 ACN:Water, 0.1% Formic acid Data was acquired on an ACQUITY® H-Class liquid chromatography system (commercially available from Waters Technologies Corporation, Milford Mass.) running isocratically at a flow rate of 0.200 mL/min. Mobile phase was comprised of 75:25 ACN:Water, 0.1% formic acid, 1 ppm citric acid. Separation performed on an ACQUITY® BEH 2.1×100 C18 column (also available from Waters Technologies Corporation, Milford, Mass.). Column temperature and sample manager temperature were set at 25 C and 30 C, respectively. Detection wavelength was performed at 200 nm using a 5 mm Ti flow cell at 20 Hz.

ACQUITY® QDa® mass detector (commercially available from Waters Technologies Corporation, Milford, Mass.) parameters were set at Probe=500 C, capillary=1.5 kV, Cone Voltage=15V, Sample rate=2 Hz. Full Scan was performed over a range of 150.0-600.0 m/z in positive mode. SIRs were collected at 201.12 m/z, 183.14 m/z, 215.12 m/z, and 197.14 m/z representing lauric acid and an internal standard as well as the parent peaks with associated water loss.

Figure 18:
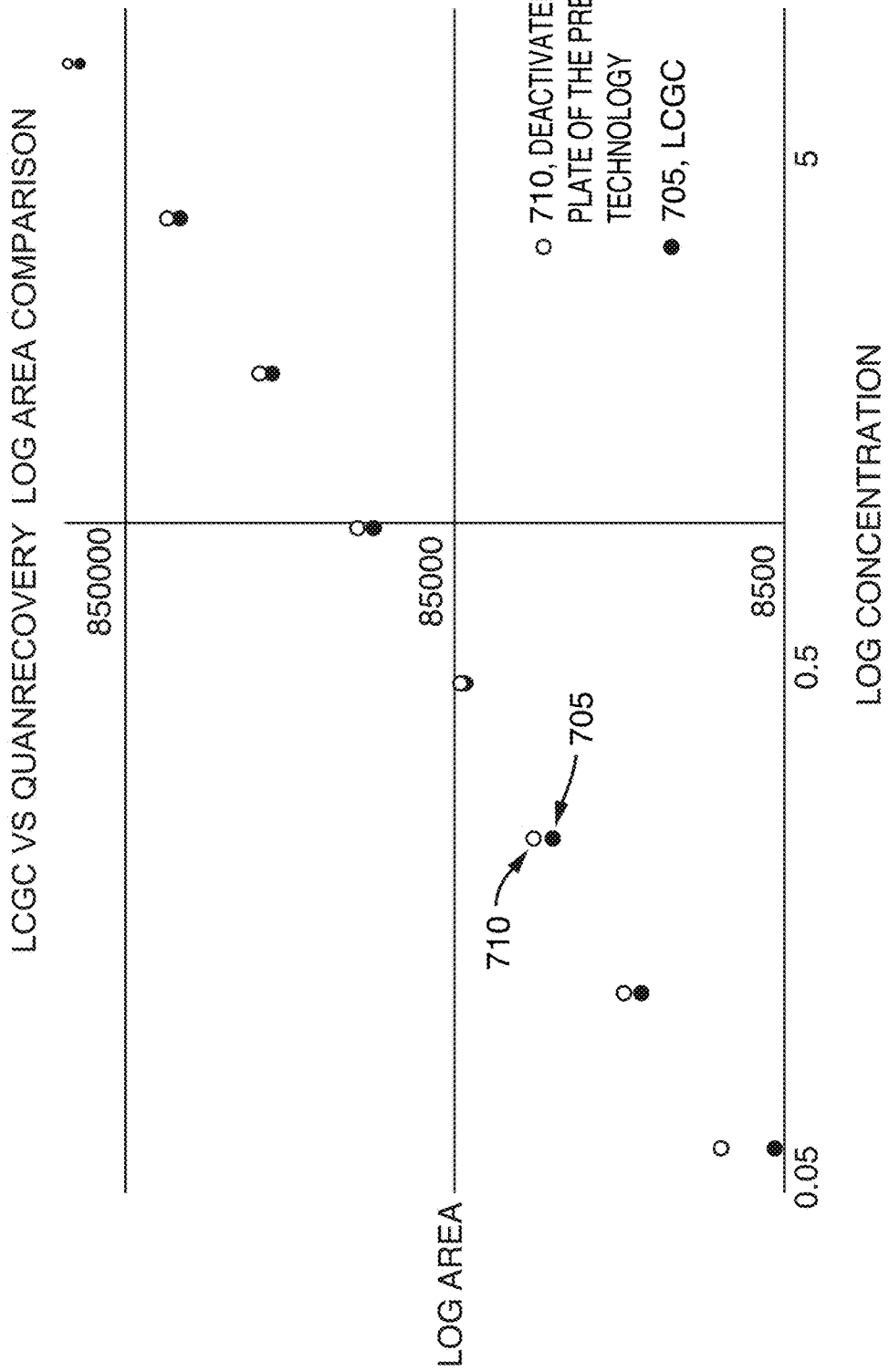
FIG. 18 is a graph showing a LOG area comparison for the LCGC certified vials and the deactivated polypropylene vials of the present technology, according to an illustrative embodiment of the technology.
Figure 19:
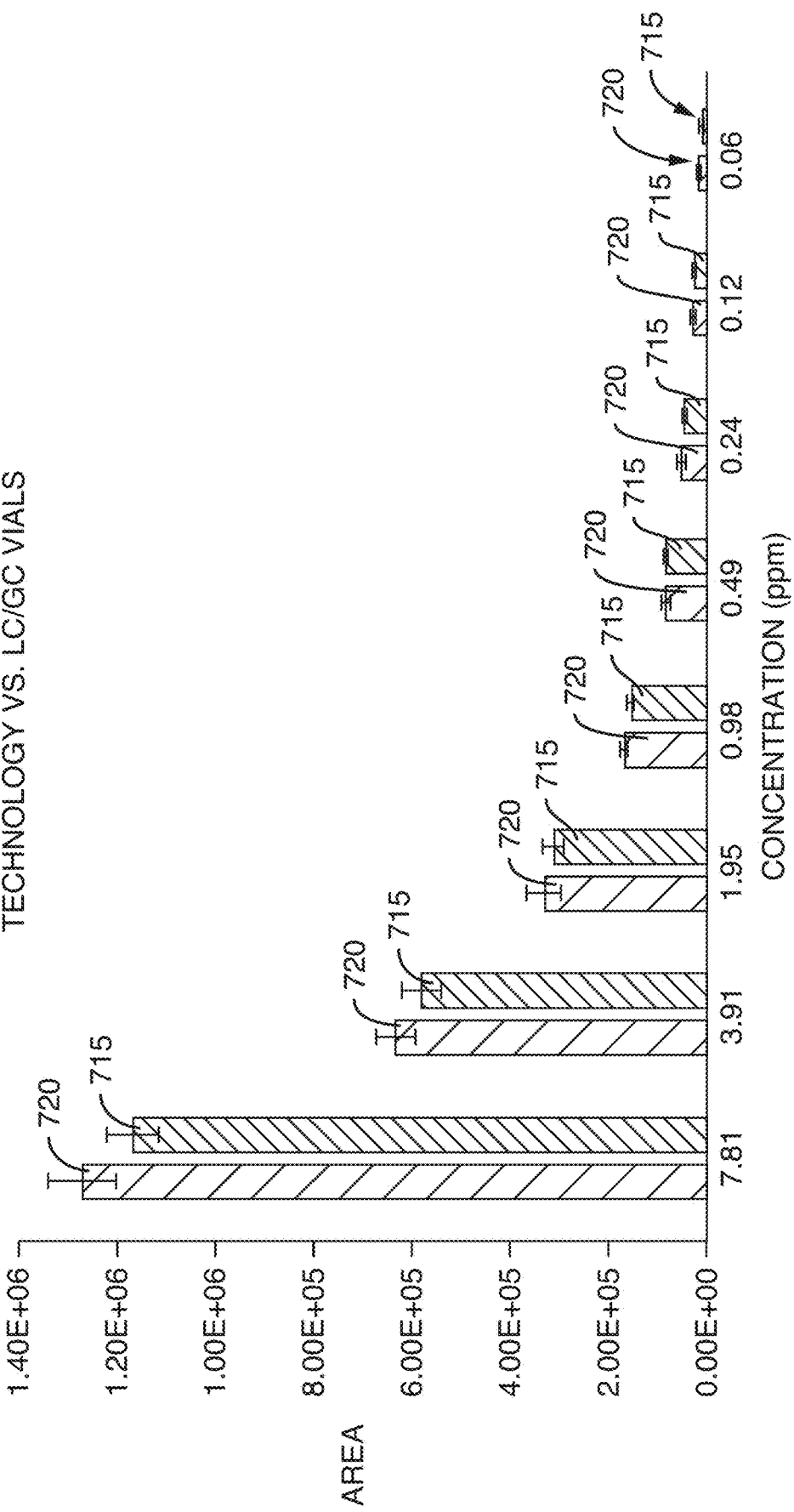
FIG. 19 is a graph showing peak area vs. concentration (ppm) for the LCGC certified vials and the deactivated polypropylene vials of the present technology, according to an illustrative embodiment of the technology.

Table 8 shows the averaged detector data (i.e., data from QDa® mass detector) from the LCGC certified vials. Table 9 shows the averaged QDa® detector data from the deactivated polypropylene vials of the present technology. FIG. 18 is a graph showing a LOG area comparison for the LCGC certified vials 705 and the deactivated polypropylene vials 710. FIG. 19 shows a graph showing peak area vs. concentration (ppm) for the LCGC certified vials 715 and the deactivated polypropylene vials 720.

TABLE 8

LCGC Certified P/N 186000327C
Averaged QDa Data
Lauric acid

| conc (ppm) | Qda Average Raw Area | Std Dev | s/n | % RSD |
|---|---|---|---|---|
| 7.8125 | 1169319 | 52689 | 26.5 | 4.51 |
| 3.90625 | 580171 | 41814 | 12.8 | 7.21 |
| 1.953125 | 310040 | 21780 | 7.3 | 7.02 |
| 0.9765625 | 152647 | 7492 | 3.7 | 4.91 |
| 0.48828125 | 79582 | 2364 | 2.0 | 2.97 |
| 0.244140625 | 42939 | 4887 | 1.1 | 11.38 |
| 0.122070313 | 23089 | 4695 | 0.6 | 20.33 |
| 0.061035156 | 9099 | 2554 | 0.3 | 28.07 |

TABLE 9

Deactivated Polypropylene Vials of the Present Technology
Averaged QDa Data
Lauric acid

| conc (ppm) | Qda Average Raw Area | Std Dev | s/n | % RSD |
|---|---|---|---|---|
| 7.8125 | 1272335 | 68612 | 28.6 | 5.39 |
| 3.90625 | 634216 | 40024 | 14.9 | 6.31 |
| 1.953125 | 328898 | 36241 | 7.2 | 11.02 |
| 0.9765625 | 164735 | 9326 | 3.6 | 5.66 |
| 0.48828125 | 81204 | 7480 | 1.9 | 9.21 |
| 0.244140625 | 49104 | 7673 | 1.1 | 15.63 |
| 0.122070313 | 26049 | 5599 | 0.5 | 21.50 |
| 0.061035156 | 13217 | 4114 | 0.3 | 31.13 |

As shown in FIG. 18 and FIG. 19, the deactivated polypropylene vials have a higher MS response overall.

Example 4: Chromatographic Fluidic Flow Path (Metal)

The process detailed in Examples 1-3 use a liquid chromatographic system. The liquid chromatographic system can have a fluidic path that is comprised predominantly of a metal surface. The metal surface can be comprised of one or more of any formulation of stainless steel, titanium or different alloys such as MP35N.

Example 5: Chromatographic Fluidic Flow Path (Non-Metal)

The process detailed in Examples 1-3 use a liquid chromatographic system. The liquid chromatographic system can have a fluidic path that is comprised predominantly of a non-metallic surface. The non-metallic surface can be comprised of one or more of any formulation of PEEK, PEEK lined steel, glass, glass lined steel, or ceramic.

Example 6: Chromatographic Fluidic Flow Path (Mixed)

The process detailed in Examples 1-3 use a liquid chromatographic system. The liquid chromatographic system can have a fluidic path that is comprised of a mixture of metallic and non-metallic surfaces. The metallic surface can be any of those of Example 4 and the non-metallic surface can be any of those of Example 5.

Example 7: Direct Analysis by MS

The process detailed in Examples 1-3 use a liquid chromatographic system. In some embodiments, the use of a chromatographic system is not necessary. Instead, the analyte sample within the deactivated vial or plate is directly administered to a mass spectroscopic analysis without the use of a liquid chromatographic separation.

Example 8: Direct Analysis by MS Via Acoustic Sampling

The process detailed in Examples 1-3 use a liquid chromatographic system. In some embodiments, the use of a chromatographic system is not necessary. Instead, the analyte sample within the deactivated vial or plate is directly administered to a mass spectroscopic analysis via acoustic sampling without the use of a liquid chromatographic separation.

Example 9: Ionization Approach

The process detailed in Examples 1-6 use a mass spectroscopic analysis. The ionization approach used for mass spectrometry, includes, but is not limited to, ESI (electrospray ionization), DESI (desorption electrospray ionization), REIMS (rapid evaporative ionization mass spectrometry) or those shown in Tables 10 and 11.

TABLE 10

Types of Atomic Mass Spectrometry

| Name | Acronym | Atomic Ion Sources | Typical Mass Analyzer |
|---|---|---|---|
| Inductively Coupled Plasma | ICPMS | High-temperature argon plasma | Quadrupole |

TABLE 10-continued

Types of Atomic Mass Spectrometry

| Name | Acronym | Atomic Ion Sources | Typical Mass Analyzer |
|---|---|---|---|
| Direct Current Plasma | DCPMS | High-temperature argon plasma | Quadrupole |
| Microwave-induced plasma | MIPMS | High-temperature argon plasma | Quadrupole |
| Spark Source | SSMS | Radio-frequency electric spark | Double-focusing |
| Thermal Ionization | TIMS | Electrically heated plasma | Double-focusing |
| Glow Discharge | GDMS | Glow-discharge plasma | Double-focusing |
| Laser Microprobe | LMMS | Focused laser beam | Time-of-flight |
| Secondary Ion | SIMS | Accelerated ion bombardment | Double-focusing |

TABLE 11

Ion Sources for Molecular Mass Spectrometry

| Basic Type | Name and Acronym | Ionizing Agent |
|---|---|---|
| Gas phase | Electron Impact (EI) | Energetic electrons |
| | Chemical Ionization (CI) | Reagent gaseous ions |
| | Field Ionization (FI) | High-potential electrode |
| Desorption | Field Desorption (FD) | High-potential electrode |
| | Electrospray Ionization (ESI) | High electrical field |
| | Matrix-assisted desorption ionization (MALDI) | Laser beam |
| | Plasma Desorption (PD) | Fission fragments from $^{252}$Cf |
| | Fast atom bombardment (FAB) | Energetic atomic beam |
| | Secondary-ion mass spectrometry | Energetic beam of ions |
| | Thermospray ionization (TS) | High temperature |

While this disclosure has been particularly shown and described with reference to example embodiments thereof, it will be understood by those skilled in the art that various changes in form and details may be made therein without departing from the scope of the technology encompassed by the appended claims. For example, other chromatography systems or detection systems can be used. In addition, the results obtained in the above examples would apply equally if not liquid chromatography system was used and direct ionization of the sample for mass spectrometry was used without separating the sample first.

What is claimed is:

1. A method of analyzing a sample comprising a fatty acid of interest, the method comprising:
    preparing an aqueous solution comprising fatty acid of interest, wherein a concentration of the fatty acid of interest is less than about 1 µM;
    placing the solution in contact with a surface of a polypropylene substrate, wherein the surface has been treated to reduce adsorption of the fatty acid of interest as compared to a non-treated surface; and
    analyzing the sample using mass spectrometry with respect to the fatty acid of interest.

2. The method of claim 1, wherein the reduction of adsorption of the fatty acid of interest is provided by a reduction in water contact angle of the surface.

3. The method of claim 2, wherein the water contact angle is reduced by at least about 1 degree.

4. The method of claim 2, wherein the water contact angle is reduced by between about 2 degrees to about 10 degrees.

5. The method of claim 2, wherein the reduced water contact angle is about 88 degrees.

6. The method of claim 2, wherein the reduced water contact angle is less than about 85 degrees.

7. The method of claim 1, wherein the reduction of adsorption of the fatty acid of interest is provided by an increase in hydrophilicity of the surface.

8. The method of claim 7, wherein the hydrophilicity is increased by about 40%.

9. The method of claim 7, wherein the hydrophilicity is increased by about 50% to about 75%.

* * * * *